| United States Patent [19] | [11] | 4,410,699 |
|---|---|---|
| Effland et al. | [45] | Oct. 18, 1983 |

[54] SUBSTITUTED 1,2,3,4-TETRAHYDRO-4-ISOQUINOLINOLS

[75] Inventors: Richard C. Effland, Bridgewater; Larry Davis, Sergeantsville; Joseph T. Klein, Bridgewater, all of N.J.

[73] Assignee: Hoechst-Roussel Pharmaceuticals Inc., Somerville, N.J.

[21] Appl. No.: 444,945

[22] Filed: Nov. 29, 1982

Related U.S. Application Data

[62] Division of Ser. No. 290,987, Aug. 7, 1981, Pat. No. 4,374,137.

[51] Int. Cl.³ .......................................... C07D 217/24
[52] U.S. Cl. .................................. 546/141; 424/258; 546/18
[58] Field of Search ........................................ 546/141

[56] References Cited

U.S. PATENT DOCUMENTS 3,745,162  7/1973  Helsley ............................. 546/141
4,166,119  8/1979  Effland et al. ..................... 424/267
4,166,120  8/1979  Effland et al. ..................... 424/267

OTHER PUBLICATIONS

Grethe, et al., "J. Org. Chem.", vol. 33, 1968, pp. 494–503.

*Primary Examiner*—Donald G. Daus
*Assistant Examiner*—James H. Turnipseed
*Attorney, Agent, or Firm*—Raymond R. Wittekind

[57] ABSTRACT

Novel spiro[benzofuranisoquinoline]s, intermediates and processes for the preparation thereof and methods for alleviating pain, inhibiting convulsions, reducing blood pressure and producing diuresis employing the compounds or compositions thereof are disclosed.

6 Claims, No Drawings

SUBSTITUTED 1,2,3,4-TETRAHYDRO-4-ISOQUINOLINOLS

This is a division of application Ser. No. 290,987 filed Aug. 7, 1981, now U.S. Pat. No. 4,374,137.

DESCRIPTION OF THE INVENTION

The present invention relates to novel spiro[benzofuranisoquinoline]s. More particularly, the present invention relates to spiro[benzofuran-2(3H),4'(2'H)-isoquinoline]s of formula 1.

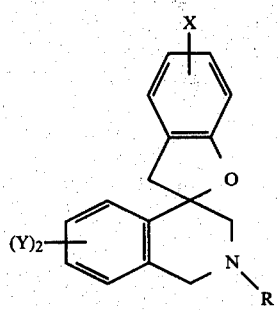

wherein Y is hydrogen or methoxy; X is hydrogen or halogen; R is hydrogen, loweralkyl, loweralkenyl, loweralkynyl, cycloalkylloweralkyl, cycloalkylcarbonyl, loweralkanoyl,

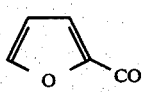

$COOR^1$ wherein $R^1$ is a loweralkyl or phenyl, $COCOOR^2$ wherein $R^2$ is loweralkyl,

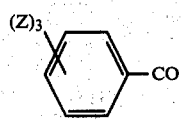

wherein Z is methoxy,

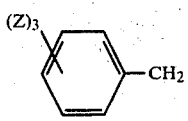

wherein Z is hydrogen or methoxy,

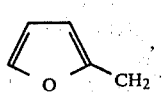

$NH_2$, NO,

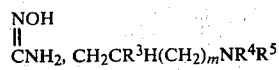

wherein $R^3$ is hydrogen or loweralkyl, m is 0 or 1, $R^4$ and $R^5$ are each independently hydrogen or loweralkyl, or $R^4$ and $R^5$ taken together with the nitrogen atom to which they are attached form a group of the formula

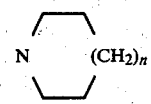

wherein n is 0 or 1,

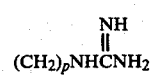

wherein p is 2, $(CH_2)_qCN$ wherein q is 0 or 1,

wherein $R^6$ is loweralkyl,

wherein $R^6$ is loweralkyl,

wherein $R^7$ is loweralkyl and $R^8$ is $(CH_2)_rNR^4R^5$ wherein $R^4$ and $R^5$ are as above and r is 2 or 3, the geometrical isomers, tautomers and optical antipodes thereof or the pharmaceutically acceptable acid addition salts thereof when R is other than cycloalkylcarbonyl, loweralkanoyl,

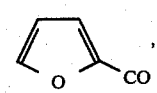

$COOR^1$ wherein $R^1$ is as above, $COCOOR^2$ wherein $R^2$ is as above,

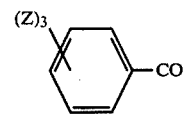

wherein Z is as above, NO, $(CH_2)_qCN$ wherein q is 0 and

wherein $R^6$ is as above and which are useful as analgesic, anticonvulsant, antihypertensive and diuretic agents, alone or in combination with inert pain alleviating, convulsion inhibiting, blood pressure reducing and diuresis producing adjuvants, respectively, as well as intermediates for the preparation thereof.

Preferred spiro[benzofuran-2(3H),4'(2'H)-isoquinoline]s of the present invention are those compounds wherein R is $CH_2CR^3H(CH_2)_mNR^4R^5$, wherein $R^3$ is hydrogen or loweralkyl, m is 0 or 1, $R^4$ and $R^5$ are each independently hydrogen or loweralkyl, or $R^4$ and $R^5$ taken together with the nitrogen atom to which they are attached form a group of the formula

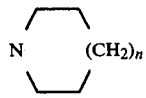

wherein n is 0 or 1, which exhibit primarily diuretic activity.

Subgeneric to the spiro[benzofuran-2(3H),4'(2'H)-isoquinoline]s of the present invention are compounds wherein:

(a) R is hydrogen, loweralkyl, loweralkenyl, loweralkynyl or cycloalkylloweralkyl;
(b) R is cycloalkylcarbonyl or loweralkanoyl;
(c) R is $COOR^1$ wherein $R^1$ is loweralkyl or phenyl, or $COCOOR^2$ wherein $R^2$ is loweralkyl;
(d) R is

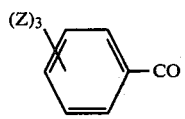

wherein Z is hydrogen or methoxy;
(e) R is

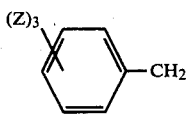

wherein Z is hydrogen or methoxy;
(f) R is

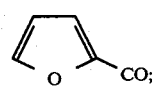

(g) R is

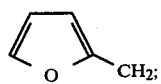

(h) R is NO;
(i) R is $NH_2$;
(j) R is

(k) R is

wherein p is 2;
(l) R is $(CH_2)_qCN$ wherein q is 0 or 1;
(m) R is

wherein $R^6$ is loweralkyl;
(n) R is

wherein $R^7$ is hydrogen or loweralkyl and $R^8$ is hydrogen or $(CH_2)_rNR^4R^5$ wherein $R^4$ and $R^5$ are each independently hydrogen or loweralkyl, or $R^4$ and $R^5$ taken together with the nitrogen atom to which they are attached form a group of the formula

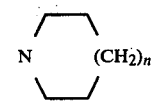

wherein n is 0 or 1, r is 2 or 3.

The present invention also relates to 1,2,3,4-tetrahydro-4-isoquinolinols of formula 2

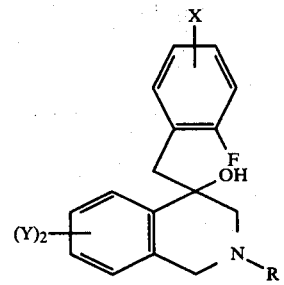

wherein R is loweralkyl or benzyl; X is hydrogen or halogen; Y is hydrogen or methoxy, useful as intermediates for the preparation of the hereinbeforementioned spiro[benzofuran-2(3H), 4'(2'H)-isoquinoline]s.

As used through the specification and appended claims, the term "alkyl" refers to a straight or branched chain hydrocarbon radical containing no unsaturation and having 1 to 10 carbon atoms such as methyl, ethyl, n-propyl, i-propyl, n-butyl, n-pentyl, isopentyl, heptyl, octyl, decyl and the like; the term "alkenyl" refers to a straight or branched chain hydrocarbon radical containing unsaturation in the form of a single carbon to carbon double bond and having from 3 to 7 carbon atoms such as propenyl, 2-butenyl, 3-ethyl-2-pentenyl, and the like; the term "alkynyl" refers to a straight or branched chain hydrocarbon radical containing unsaturation in the form of a single carbon to carbon triple bond and having from 3 to 7 carbon atoms such as 2-propynyl, 2-butynyl, 1-methyl-2-butynyl, 4-methyl-2-pentynyl, 4,4-dimethyl-2-butynyl and the like; the term "cycloalkyl" refers to a saturated hydrocarbon group possessing at least one carbocyclic ring, the ring containing from 3 to 10 carbon atoms such as cyclopropyl, cyclobutyl, cyclopentyl, cyclohexyl, cyclooctyl, 1-adamantyl and the like; the term "alkoxy" refers to a monovalent substituent which consists of an alkyl group linked through an ether oxygen and having its free valence bond from the ether oxygen such as methoxy, thoxy, isopropoxy, n-butoxy, tert-butoxy, n-pentoxy, isopentoxy, heptoxy, hexoxy, octoxy, decoxy and the like; the term "alkanol" refers to a compound formed by combination of an alkyl group and hydroxy radical. Examples of alkanols are methanol, ethanol, n- and i-propanol, 2,2-dimethylethanol, hexanol, octanol, decanol and the like. The term "alkanoic acid" refers to a compound formed by combination of a carboxyl group with a hydrogen atom or alkyl group. Examples of alkanoic acids are formic acid, acetic acid, propanoic acid, 2,2-dimethylacetic acid, hexanoic acid, octanoic acid, decanoic acid and the like; the term "halogen" refers to a member of the family fluorine, chlorine, bromine or iodine. The term "alkanoyl" refers to the radical formed by removal of the hydroxyl function from an alkanoic acid. Examples of alkanoyl groups are formyl, acetyl, propionyl, 2,2-dimethylacetyl, hexanoyl, octanoyl, decanoyl and the like. The term "aryl" denotes a phenyl group substituted by three methoxy functions, or a furyl group. The term "aroic acid" refers to a compound formed by combination of a carboxyl group with an aryl function. The term "aroyl" refers to the radical formed by removal of the hydroxyl function from an aroic acid. The term "lower" as applied to any of the aforementioned groups refers to a group having a carbon skeleton containing up to and including 7 carbon atoms.

The compounds of the present invention which lack an element of symmetry exist as optical antipodes and as the racemic forms thereof. The optical antipodes may be prepared from the corresponding racemic forms by standard optical resolution techniques, involving, for example, the separation of diastereomeric salts of those instant compounds characterized by the presence of a basic amino group and an optically active acid, or by the synthesis from optically active precursors.

The amidines, guanidines and thiocarbamyl compounds of the present invention, i.e, the compounds wherein R is

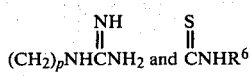

wherein $R^6$, $R^7$, $R^8$ and p are as hereinbefore described exist in equilibrium with the corresponding tautomers, i.e, with compounds wherein R is

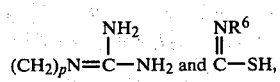

respectively.

The present invention comprehends all optical isomers and racemic forms thereof of the compounds disclosed and claimed herein and the formulas of the compounds shown herein are intended to encompass all possible tautomers and optical isomers of the compounds so depicted.

The novel spiro[benzofuran-2(3H),4'(2'H)-isoquinoline]s of the present invention may be prepared from 2,3-dihydro-4(1H)-isoquinolones of formula 3 by the series of processes illustrated in Reaction Schemes 1 to 4.

To prepare the parent ring system 7, i.e., the spiro[benzofuran-2(3H),4'(2'H)-isoquinoline] 1 wherein R is hydrogen, a 2,3-dihydro-4(1H)isoquinoline 3 wherein R is loweralkyl or benzyl is treated with a Grignard reagent 4, prepared from a 2-fluorobenzyl chloride or 2-fluorobenzyl bromide by conventional methods, to afford the 1,2,3,4-tetrahydro-4-isoquinolinol 2, which is cyclized to the spiro[benzofuran-2(3H),4'(2'H)-isoquinoline] 5, wherein R is loweralkyl or benzyl and dealkylated or debenzylated to spiro[benzofuran-2(3H),4'(2'H)-isoquinoline] 7, via the alkoxycarbonyl or phenoxycarbonyl derivative 6 wherein $R^1$ is loweralkyl or phenyl, respectively. (See Reaction Scheme I).

The initial step of this sequence (illustrated in Reaction Scheme I) is conveniently performed by contacting the preformed Grignard reagent 4 in situ with the isoquinolone 3 in an ethereal solvent such as diethyl ether, dioxane or tetrahydrofuran, diethyl ether being preferred. While the Grignard temperature is not narrowly critical, it is preferred to heat the mixture under reflux to complete the reaction.

The cyclization of isoquinolinol 2 to spiro[benzofuranisoquinoline] 5 is readily accomplished by treating the former with a base such as an alkali metal hydride, for example, lithium hydride, sodium hydride or potassium hydride, in a mixed solution comprising of an aromatic hydrocarbon such as, for example, benzene, toluene or xylene, and a polar aprotic substance, such as for example, dimethylacetamide, dimethylformamide and hexamethylphosphoramide, at the reflux temperature of the system. At this temperature, which is not critical, the cyclization proceeds at a reasonable rate. Sodium hydride is the preferred alkali metal hydride. A mixture of benzene or toluene and dimethylformamide is the preferred solvent system.

The dealkylation or debenzylation of 5 to 7 via carbamate 6 is achieved by contacting the N-alkyl- or N-benzylspiro[benzofuranisoquinoline] 5 with a loweralkyl haloformate or phenyl haloformate of formula 8 wherein $R^1$ is loweralkyl or phenyl, respectively, and Hal is bromo or chloro in an aromatic hydrocarbon solvent such as benzene, toluene or xylene, or a chlorocarbon solvent such as chloroform, dichloromethane or dichloroethane. Among the aromatic hydrocarbons, benzene is preferred. Among the chlorocarbon solvents, dichloromethane is preferred.

The temperature at which the dealkylation or debenzylation reaction is performed is not crucial. It is preferred, however, to perform the reaction at a temperature such that the carbamate 6 is formed at a reasonable rate.

While not essential, an acid scavenger such as an alkali metal carbonate (potassium carbonate) or bicarbonate (sodium bicarbonate) may be employed in the dealkylation and debenzylation reactions.

The carbamate 6, so obtained, is converted to spiro[benzofuranisoquinoline] 7 by techniques well known in the art. For example, carbamate 6 may be hydrolyzed to 7 by treatment with alkali metal hydroxides such as lithium hydroxide, sodium hydroxide or potassium hydroxide in refluxing aqueous alkanols such as aqueous methanol, aqueous ethanol or aqueous 1- or 2-propanol.

Derivatives of the parent ring system, i.e., derivatives of spiro[benzofuran-2(3H),4'(2'H)-isoquinoline] 7, are prepared from the nitrogen unsubstituted compound 7 by the processes outlined in Reaction Schemes II to IV.

To prepare the carboxamine 11 of Reaction Scheme II, the parent compound 7 is first treated with a cyanogen halide 9 such as cyanogen bromide or cyanogen chloride, preferably cyanogen bromide, in the presence of an acid-acceptor such as sodium or potassium carbonate or sodium or potassium bicarbonate, preferably potassium carbonate, in a halocarbon solvent such as dichloromethane, trichloromethane or dichloroethane, preferably trichloromethane, at a temperature to assure a reasonable rate of conversion, preferably at the reflux temperature of the system to afford the N-cyano derivative 10. The N-cyano compound 10, so obtained, is then contacted with hydroxylamine hydrochloride in a polar aprotic solvent such as dimethylacetamide, dimethylformamide or hexamethylphosphoramide, preferably dimethylformamide, in the presence of an acid-acceptor such as sodium or potassium carbonate or sodium or potassium bicarbonate, preferably sodium carbonate, at a reaction temperature within the range from about 25° to about 110° C., preferably a reaction temperature of about 105° C.

To prepare the N-amino derivative 18 of Reaction Scheme II, the 2'-unsubstituted spiro[benzofuranisoquinoline] 7 is nitrosated by means of an alkali metal nitrite such as sodium nitrite or potassium nitrite, sodium nitrite being preferred, in an alkanoic acid such as acetic acid or propionic acid, acetic acid being preferred, to provide the N-nitroso derivative 17, which is reduced to 18 by a metal such as zinc or tin, zinc being preferred, in aqueous acetic acid or aqueous propionic acid. The reaction temperatures at which the nitrosation and reduction are performed are not crucial to the success of the process. Reaction temperatures in the range of from about 0° to about 25° C. are preferred.

To prepare the N-oxalyl 16 and N-acyl (alkanoyl, cycloalkylcarbonyl and aroyl) derivatives 13 of the N-unsubstituted isoquinoline 7 shown in Reaction Scheme II, the parent spiro[benzofuranisoquinoline] 7 is condensed, respectively, with a alkyloxalyl halide or an acyl halide, preferably the chlorides, in a halocarbon solvent such as dichloromethane or trichloromethane in the presence of an acid-scavenger such as sodium or potassium bicarbonate, sodium or potassium carbonate or a tertiary amine such as, for example, triethylamine, trimethylamine or pyridine. In the former process, i.e., the process for the synthesis of the oxalyl derivatives, 16, trichloromethane and sodium bicarbonate are the preferred solvent and acid scavenger. In the latter process, i.e., the process for the synthesis of the acyl derivatives 13, the preferred solvent and acid scavenger are dichloromethane and triethylamine. The condensation proceeds smoothly at about 25° C. In the case of the N-oxalyl compound, the mixture may be heated under reflux to promote completion of the reaction.

The acyl derivatives 13 of the parent spiro[benzofuran-2(3H),4'(2'H)-isoquinoline] 7, i.e., the compounds of formula 13 wherein $R^9$ is loweralkyl, cycloalkyl,

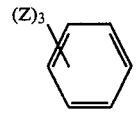

wherein Z is methoxy, or

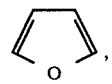

are reduced by alkali metal aluminum hydrides such as lithium aluminum hydride or sodium aluminum hydride in a refluxing ethereal solvent such as diethyl ether, tetrahydrofuran or dioxane to the N-alkyl, N-cycloalkylalkyl and N-aralkyl derivatives of the parent system 7 wherein R is as above of the parent system 1. Lithium aluminum hydride in tetrahydrofuran is preferred.

Reaction Scheme III delineates additional processes for the synthesis of 2'-derivatives of spiro[benzofuran-2(3H),4'(2'H)-isoquinolines] 7.

To synthesize the alkenyl 19 and alkynyl 21 derivatives of the parent isoquinoline 7, the 2'-unsubstituted precursor 7 is contacted with the alkenyl and alkynyl halides 18 and 20, respectively, in an alkanol such as ethanol, 2-propanol or n-butanol, n-butanol being preferred, in the presence of an acid acceptor such as sodium or potassium carbonate or sodium or potassium bicarbonate, potassium carbonate being preferred, and a displacement promoter such as potassium iodide. The reaction temperature is now narrowly critical. It is preferred, however, to heat the reaction under reflux to assure a reasonable rate of conversion.

To fabricate the dialkylaminoalkyl derivative 23 of the basic system 7, the N-unsubstituted isoquinoline 7 is treated with an aminoalkyl halide 22, the chloride being preferred, in an alkanol such as, for example, ethanol, 2-propanol or n-butanol, containing a displacement promoter such as, for example, potassium iodide, in the presence of an acid scavenger such as sodium or potassium carbonate or bicarbonate. n-Butanol is the preferred solvent and potassium carbonate is the preferred acid acceptor. While the reaction temperature is not crucial, it is preferred to perform the reaction at the reflux temperature of the system to assure a reasonable rate conversion.

Dialkylaminoalkyl derivatives 23 of spiro[benzofuranisoquinoline] 7 are dealkylated to monoalkylaminoalkyl derivatives 25 of 7 by treatment with 2,2,2-trichloroethyl chloroformate in an aromatic hydrocarbon solvent such as benzene, toluene or xylene, benzene being preferred, in the presence of an acid acceptor such as sodium or potassium carbonate or bicarbonate, potassium carbonate being preferred, followed by treatment of the intermediate so formed with a metal such as zinc or tin, zinc being preferred, in an alkanoic acid such as acetic or propionic acid, acetic acid being preferred. The initial phase of the reaction is generally performed at the reflux temperature of the reaction mixture and the final phase is generally conducted at about room temperature, although the reaction temperatures are not critical.

To form the N-amidino derivative 24 of the parent isoquinoline 7, the cyclic amine 7 is treated with 3,5- dimethylpyrazole carboxamidine nitrate in an aqueous alkanol such as aqueous ethanol or aqueous 2-propanol, aqueous ethanol being preferred, 95% ethanol being most preferred, at the reflux temperature of the reaction mixture. The reaction also proceeds readily at lower temperatures. However, the elevated temperature ensures a reasonable rate of conversion.

Additional derivatives of spiro[benzofuran-2(3H),4'(2'H)-isoquinoline] 7 are prepared by the processes depicted in Reaction Scheme IV.

To prepare aminoalkyl derivatives 28 of the N-unsubstituted parent 7, the secondary amine 7 is treated with a cyanoalkyl halide 26, preferably the chloride, in a polar aprotic solvent such as dimethylacetamide, dimethylformamide or hexamethylphosphoramide, preferably dimethylformamide, containing an acid acceptor such as sodium or potassium carbonate or bicarbonate, preferably sodium bicarbonate, to afford cyanoalkyl derivative 27, which in turn is reduced with an alkali metal aluminum hydride such as sodium aluminum hydride or lithium aluminum hydride in an ethereal solvent such as diethyl ether, tetrahydrofuran or dioxane, preferably lithium aluminum hydride in tetrahydrofuran. The cyanoalkylation and reduction are generally performed at the reflux temperature of the reaction system, even though this temperature is not narrowly critical and the reaction proceeds smoothly at lower temperatures.

The aminoalkyl derivative 28 of spiro[benzofuranisoquinoline] 7 is converted to guanidinoalkyl derivative 29 by treatment with 2-methyl-2-thiopseudourea sulfate in a suitable solvent. Among suitable solvents there may be mentioned aqueous alkanols such as aqueous ethanol and aqueous 2-propanol, aqueous ethanol being preferred. To promote the conversion, the reaction mixture is preferably heated at the reflux temperature of the system.

The N,S-dialkylthiocarbamyl derivative 33 of spiro[benzofuranisoquinoline] 7 is prepared by condensing the parent compound 7 with an alkylisothiocyanate 30 of the N-alkylthiocarbamyl derivative 31 and alkylating the thiocarbamyl compound 31, so formed, with an alkyl halide 32. The condensation is conveniently performed in an aromatic hydrocarbon solvent such as benzene, toluene or xylene, preferably benzene, at ambient temperature. The alkylation is generally performed in an alkanol such as methanol, ethanol or 2-propanol or mixtures thereof, mixtures of methanol and ethanol being preferred, at the reflux temperature of the reaction mixture, at which temperature the conversion proceeds at a reasonable rate.

To prepare the aminoalkylamidino derivative 35 of the parent system 7, spiro[benzofuranisoquinoline] 33 is treated with dialkylaminoalkylamine 34 in a suitable solvent at the reflux temperature of the system. Suitable solvents include alkanols such as methanol, ethanol and 2-propanol. Ethanol is preferred. The reaction also proceeds satisfactorily at lower temperatures, the higher temperatures being employed to promote the reaction rate.

The requisite 2,3-dihydro-4(1H)-isoquinolones 3 may be prepared from readily available benzaldehydes 36 by the process disclosed in G. Grethe, et al., J. Org. Chem., 33, 494(1963) or processes related thereto. See Reaction Scheme V.

For example, 3,4-dimethoxybenzaldehyde 36 (Y is methoxy) is reduced by either the Wolff-Kischner or Clemmensen methods to 3,4-dimethoxytoluene 37 (Y is methoxy), which is acylated by the Freidel-Crafts technique to 4,5-dimethoxy-2-methylacetophenone 38 (Y is methoxy) and oxidized by hypohalite to 4,5-dimethoxy-2-methylbenzoic acid 39 (Y is methoxy). The acid 39 (Y is methoxy) is esterified to ethyl 4,5-dimethoxy-2-methylbenzoate-40 (Y is methoxy), which is brominated by N-bromoimides to ethyl 2-bromomethyl-3,4-dimethoxybenzoate 41 (Y is methoxy) and condensed with the ethyl ester sarcosine 43 (R is methyl), prepared by esterification of sarcosine 42 (R is methyl, to N-(2-carbethoxy-4,5-dimethoxybenzyl)sarcosine ethyl ester 44 (R is methyl and Y is methoxy) and cyclized to 2,3-dihydro-6,7-dimethoxy-4(1H)isoquinolone 3 (R is methyl, Y is methoxy).

The requisite Grignard reagents 4 are prepared either from commercially available or readily obtainable 2-fluorobenzyl halides by conventional methods. See Reaction Scheme VI.

For example, 4-chloro-6-fluorotoluene 45 (X is 4-Cl) and bromine are irradiated to afford 4-chloro-6-fluorobenzyl bromide 47 (X is 4-Cl and Hal is Br) which is contacted with magnesium under the usual conditions, namely, in an ethereal solvent such as diethyl ether, in the presence of an initiator such as iodine, to provide Grignard reagent 4. (X is 4-Cl and Hal is Br).

The spiro[benzofuranisoquinoline]s of the present invention are useful as diuretics due to their ability to produce diuresis in mammals.

Diuretic activity is determined in rats by a metod similar to that described by C. M. Kagawa and M. J. Kalm, Arch. Intern. Pharmacodyn., 137, 241 (1962). The test compound is administered orally to a group of rats and the average volume of urine excreted and sodium produced is measured. One gram per kilogram of body weight of urea, a known diuretic agent, is administered orally to a positive control group of rats and the average volume of urine excreted and sodium produced is measured. Diuretic activity expressed as the ratio of the average volume of urine excreted or sodium produced in the test group to the average volume of urine excreted or sodium produced in the control group (a ratio greater than 1 indicates diuretic activity) of some of the instant spiro[benzofuranisoquinoline]s as well as standard diuretics is presented in Table I.

TABLE I

| COMPOUND | DOSE (mg/kg of body weight) | DIURESIS PRODUCTION (test compound/urea) | SODIUM PRODUCTION (test compound/urea) |
|---|---|---|---|
| 2'-Carboxamidoximespiro-[benzofuran-2(3H),4'(2'H)-isoquinoline] hydrochloride | 50 | 1.0 | 1.5 |
| 2'-Methylspiro[benzofuran-2(3H),4'(2'H)-isoquinoline] hydrochloride | 15 | 1.0 | 2.5 |
| 6',7'-Dimethoxy-2'-propyl-spiro[benzofuran-2(3H),4'(2'H)- | 50 | 1.4 | 1.0 |

TABLE I-continued

| COMPOUND | DOSE (mg/kg of body weight) | DIURESIS PRODUCTION (test compound/urea) | SODIUM PRODUCTION (test compound/urea) |
|---|---|---|---|
| isoquinoline] | | | |
| 6-Chloro-2'-(3-piperidino-propyl)-spiro[benzofuran-2(3H),4'(2'H)-isoquinoline] dihydrochloride | 10 | 1.6 | 3.4 |
| 6-Chloro-2'-(3-N,N—dimethylamino-2-methylpropyl)-spiro[benzofuran-2(3H),4',(2'H)-isoquinoline] dioxalate | 5 | 1.1 | 2.0 |
| 6',7'-Dimethoxy-2'-(3-N,N—dimethylaminopropyl)-spiro[benzofuran-2(3H),4'(2'H)-isoquinoline] dihydrochloride | 50 | 1.1 | 2.7 |
| 2'-(3-N,N—Dimethylaminopropyl)-spiro[benzofuran-2(3H),4'(2'H)-isoquinoline] dihydrochloride | 10 | 2.3 | 1.9 |
| 2'-(2-N,N—Diethylaminoethyl)-spiro[benzofuran-2(3H),4'(2'H)-isoquinoline] dihydrochloride | 25 | 1.4 | 2.5 |
| 6-Chloro-2'-(2-N,N—diethyl-aminoethyl-spiro[benzofuran-2(3H),4'(2'H)-isoquinoline] dihydrochloride | 50 | 1.0 | 1.8 |
| 2'-(3-N—Methylaminopropyl)-spiro[benzofuran-2(3H),4'(2'H)-isoquinoline] dihydrochloride | 25 | 1.4 | 3.0 |
| 2'-Amidinospiro[benzofuran-2(3H),4'(2'H)-isoquinoline] nitrate | 50 | 1.0 | 1.2 |
| 2'-(2-Aminoethyl)-spiro[benzofuran-2(3H),4'(2'H)-isoquinoline] dihydrochloride | 8 | 1.6 | 1.5 |
| ethacrynic acid | 64 | 2.5 | |
| tienilic acid | 64 | 1.8 | |
| hydrochlorothiazide | 50 | | 1.9 |
| amiloride | 50 | | 1.4 |

Diuresis production is achieved when the present spiro[benzofuranisoquinoline]s are administered to a subject requiring such treatment as an effective oral, parenteral or intravenous dose of from 0.01 to 100 mg/kg of body weight per day. A particularly effective amount is about 25 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and that they do not, to any extent, limit the scope or practice of the invention.

The spiro[benzofuranisoquinoline] of the present invention are also useful as antihypertensives due to their ability to reduce blood pressure in mammals. Antihypertensive activity is measured in the spontaneous hypertensive rat by the indirect tail cuff method described by A. Schwartz, Ed., "Methods in Pharmacology," Vol. 1, Appleton-Century-Crofts, New York, N.Y., 1971, page 135. According to this procedure, the test compound is administered orally to a group of 5 rats for 3 days in relation to a control group of the same number. The decrease in blood pressure is measured on the third day of administration. The antihypertensive activity expressed as the decrease in mean arterial blood pressure (mm of mercury) in this procedure of some of the compounds of the present invention is presented in Table II.

TABLE II

| COMPOUND | DOSE mg/kg of body wgt | BLOOD PRESSURE DECREASE (mm/mercury) |
|---|---|---|
| 2'-(2-N,N—Diethylaminoethyl)-spiro[benzofuran-2(3H),4'(2'H)-isoquinoline] | 50 | 42 |
|  | 25 | 35 |
| 6-Chloro-2'-(3-piperidino-propyl)spiro[benzofuran-2(3H),4'(2'H)-isoquinoline] dihydrochloride | 50 | 28 |
| 6-Chloro-2'-(3-N,N—dimethylamino-2-methylpropyl)-spiro[benzofuran-2(3H),4'(2'H)-isoquinoline] dioxalate | 50 | 16 |
| 2'-(3-Methyl-2-butenyl)-spiro[benzofuran-2(3H),4'(2'H)-isoquinoline] hydrochloride | 50 | 16 |
| 2'-(Cyclopropylmethyl)-spiro[benzofuran-2(3H),4'(2'H)-isoquinoline] hydrochloride | 50 | 30 |
| 2'-(3,4,5-Trimethoxybenzyl-spiro[benzofuran-2(3H),4'(2'H)-isoquinoline] hydrochloride | 50 | 29 |
| 2'-(2-Propynyl)-spiro[benzofuran-2(3H),4'(2'H)-isoquinoline] oxalate | 50 | 27 |
| 4-(2-Fluorobenzyl)-6,7-dimethoxy-2-methyl-1,2,3,4-tetrahydro-4-isoquininolinol | 50 | 26 |
| 2'-(2-Guanidinoethyl)-spiro[benzofuran-2(3H),4'(2'H)-isoquinoline] hemisulfate | 50 | 19 |
| 6',7'-Dimethoxyspiro[benzofuran-2(3H),4'(2'H)-isoquinoline] maleate | 50 | 23 |
| 6',7'-Dimethoxy-2'-(3-N,N— | 50 | 19 |

TABLE II-continued

| COMPOUND | DOSE mg/kg of body wgt | BLOOD PRESSURE DECREASE (mm/mercury) |
|---|---|---|
| dimethylaminopropyl)-spiro[benzofuran-2(3H),4'(2'H)-isoquinoline] dihydrochloride | | |
| 2'-(N—Methylthiocarbamyl)-spiro[benzofuran-2(3H),4'(2'H)-isoquinoline] | 50 | 20 |
| clonidine | 50 ug/kg | 20 |
| guanethidine | 50 | 20 |

Blood pressure reduction is achieved when the present spiro[benzofuranisoquinoline]s are administered to a subject requiring such treatment as an effective oral, parenteral or intravenous dose of from 0.01 to 50 mg/kg of body weight per day. A particularly preferred effective amount is about 25 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and that they do not, to any extent, limit the scope or practice of the invention.

The spiro[benzofuranisoquinoline]s of the present invention are also useful as anticonvulsants due to their ability to inhibit convulsions in mammals.

Anticonvulsant activity is determined in male mice by a method similar to that described by L. A. Woodbury and U. D. Davenport in Arch Intern. Pharmacodyn., 92, 97(1952). The test compound is administered in a vehicle intraperitoneally to a group of six mice and the number of mice protected from the effects of supramaximal electric shock, i.e., the number of mice not exhibiting extensor tonus is observed at 30, 60 and 120 minute time intervals post administration. Anticonvulsant activity is expressed as the normalized percent inhibition of supramaximal electroshock effects of the test group in relation to the supramaximal electroshock effect of a control group of mice given only the vehicle. The anticonvulsant activity of some spiro[benzofuranisoquinoline]s of the present invention is presented in Table III.

TABLE III

| COMPOUND | DOSE mg/kg of body wgt. | INHIBITION % |
|---|---|---|
| Spiro[benzofuran-2(3H),4'(2'H)-isoquinoline] hydrochloride | 50 | 50 |
| 6-Chloro-2'-methyl-spiro[benzofuran-2(3H),4'(2'H)-isoquinoline] hydrochloride | 50 | 100 |
| 6-Chlorospiro[benzofuran-2(3H),4'(2'H)-isoquinoline] hydrochloride | 40.9 | 50 |
| 6-Chloro-2'-(3-piperidinopropyl)spiro[benzofuran-2(3H),4'(2'H)-isoquinoline] dihydrochloride | 50 | 100 |
| 6-Chloro-2'-(3-N,N—dimethyl-amino-2-methylpropyl)-spiro[benzofuran-2(3H),4'(2'H)-isoquinoline] dioxalate | 50 | 100 |
| 6',7'-Dimethoxy-2'-propyl-spiro[benzofuran-2(3H),4'(2'H)-isoquinoline] hydrochloride | 50 | 50 |
| 6-Chloro-2'-(2-N,N— | 50 | 67 |

TABLE III-continued

| COMPOUND | DOSE mg/kg of body wgt. | INHIBITION % |
|---|---|---|
| diethylaminoethyl)-spiro[benzofuran-2(3H),4'(2'H)-isoquinoline] dihydrochloride | 50 | 67 |
| Chlorodiazepoxide (standard) | 8.0 | 50 |
| Diazepam (standard) | 1.7 | 50 |

Convulsion inhibition is achieved when the present spiro[benzofuranisoquinoline]s are administered to a subject requiring such treatment as an effective oral, parenteral or intravenous dose of from 0.01 to 100 mg/kg of body weight per day. A particularly effective amount is about 25 mg/kg of body weight per day. It is to be understood, however, that for any particular subject, specific dosage regimens should be adjusted according to the individual need and the professional judgment of the person administering for supervising the administration of the aforesaid compound. It is to be further understood that the dosages set forth herein are exemplary only and that they do not, to any extent, limit the scope or practice of the invention.

The spiro[benzofuranisoquinoline]s of the present invention are useful as analgesic agents due to their ability to alleviate pain in mammals which is demonstrated in the phenyl-para-quinone writhing assay in mice, a standard assay for analgesia [Proc. Soc. Exptl. Biol. Med., 95, 729 (1953)]. Presented in Table IV is the analgesic effect of some of the compounds of the invention, expressed as percent inhibition of phenyl-para-quinone induced writhing.

TABLE IV

| COMPOUND | DOSE (subcutaneous mg/kg of body wgt) | INHIBITION % |
|---|---|---|
| N—Benzylspiro[benzofuran-2(3H),4'(2'H)-isoquinoline] hydrochloride | 25 | 31 |
| Spiro[benzofuran-2(3H),4'(2'H)-isoquinoline] hydrochloride | 25 | 35 |
| 2'-(3-Methyl-2-butenyl)-spiro[benzofuran-2(3H),4'(2'H)-isoquinoline] hydrochloride | 25 | 35 |
| 2'-Cyclopropylmethyl-spiro[benzofuran-2(3H),4'(2'H)-isoquinoline] hydrochloride | 25 | 62 |
| 2'-(n-Propyl)-spiro[benzofuran-2(3H),4'(2'H)-isoquinoline] hydrochloride | 12.6 | 50 |
| 2'-(3,4,5-Trimethoxybenzoyl)-spiro[benzofuran-2(3H),4'(2'H)-isoquinoline] | 25 | 49 |
| 2'-(3,4,5-Trimethoxybenzyl)-spiro[benzofuran-2(3H),4'(2'H)-isoquinoline] hydrochloride | 25 | 50 |
| 2'-Ethylspiro[benzofuran-2(3H),4'(2'H)-isoquinoline] hydrochloride | 25 | 65 |
| 2'-(2-N,N—Diethylaminoethyl)-spiro[benzofuran-2(3H),4'(2'H)-isoquinoline] dihydrochloride | 25 | 31 |
| 2'-(2-Propynyl)-spiro[benzofuran-2(3H),4'(2'H)-isoquinoline] oxalate | 25 | 27 |
| 2'-(2-Furanylmethyl)-spiro[benzofuran-2(3H),4'(2'H)-isoquinoline] hydrochloride | 25 | 30 |
| 2'-Amidinospiro[benzofuran-2(3H),4'(2'H)-isoquinoline] nitrate | 25 | 34 |
| 2'-(3-N,N—Dimethylaminopropyl)- | 25 | 33 |

TABLE IV-continued

| COMPOUND | DOSE (subcutaneous mg/kg of body wgt) | INHIBITION % |
|---|---|---|
| spiro[benzofuran-2(3H),4'(2'H)-isoquinoline] dihydrochloride | | |
| 4-(2-Fluorobenzyl)-6,7-dimethoxy-2-methyl-1,2,3,4-tetrahydro-4-isoquinilinol | 25 | 55 |
| 2'-(N—Methylthiocarbamyl-spiro[benzofuran-2(3H),4'(2'H)-isoquinoline] | 25 | 60 |
| 6',7'-Dimethoxyspiro[benzofuran-2(3H),4'(2'H)-isoquinoline] maleate | 25 | 52 |
| 6-Chloro-2'-(3-N,N—dimethylamino-2-methylpropyl)spiro[benzofuran-2(3H),4'(2'H)-isoquinoline] dioxalate | 25 | 62 |
| 6',7'-Dimethoxy-2'-propyl-spiro[benzofuran-2(3H),4'(2'H)-isoquinoline] hydrochloride | 25 | 53 |
| 6',7'-Dimethoxy-2'-[N'—methyl-N—(3-dimethylaminopropyl)]amidino-spiro[benzofuran-2(3H),4'(2'H)-isoquinoline] dinitrate | 25 | 46 |
| 6-Chloro-2'-(2-N,N—diethylamino-ethyl)spiro[benzofuran-2(3H),4'(2'H)-isoquinoline] dihydrochloride | 25 | 46 |
| 2'-Aminospiro[benzofuran-2(3H),4'(2'H)-isoquinoline] hydrochloride | 25 | 32 |
| propoxyphene | 3.9 | 50 |
| pentazocin | 1.3 | 50 |

Analgesia production is achieved when the present spiro[benzofuranisoquinoline]s are administered to a subject requiring such treatment as an effective oral, parenteral or intravenous dose of from 0.01 to 100 mg/kg of body weight per day. A particularly effective amount is about 25 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and that they do not, to any extent, limit the scope or practice of the invention.

EXAMPLES

The following Examples are for illustrative purposes only and are not to be construed as limiting the invention. All temperatures are in degrees centigrade (°C.).

EXAMPLE 1

2-Benzyl-4-(2-fluorobenzyl)-1,2,3,4-tetrahydro-4-isoquinolinol hydrochloride

To a suspension of magnesium shavings (2.7 g) and a crystal of iodine in anhydrous ether (25 ml) is added several milliliters of a total of 14.5 g 2-fluorobenzyl chloride. After initiation of the reaction with a hot air gun, the remainder of the 2-fluorobenzyl chloride is added dropwise as a solution in ether (75 ml). After the addition is complete, the reaction mixture is refluxed for 15 minutes. A solution of 2-benzyl-2,3-dihydro-4(1H)-isoquinolone (23.7 g) in ether (100 ml) is added dropwise at room temperature. The granular precipitate which forms is stirred at room temperature, filtered and washed with ether. The solid is hydrolyzed by stirring at room temperature with an ammonium chloride solution for one hour, followed by ether extraction. After washing the ether solution with saturated sodium chloride solution and drying over anhydrous magnesium sulfate, the ether is removed to give a brown oil. The oil is dissolved in ether and added to ethereal hydrogen chloride to give a hydrochloride salt. Recrystallization from acetone and from isopropanol/methanol provides 13.9 g (36%) of product as crystals, mp 192°–194°.

ANALYSIS: Calculated for $C_{23}H_{22}FNO \cdot HCl$ 71.95%C 6.05%H 3.65%N Found: 71.68%C 6.14%H 3.66%N

EXAMPLE 2

N-Benzylspiro[benzofuran-2(3H),4'(2'H)-isoquinoline]-hydrochloride

Sodium hydride (0.52 g 50% oil dispersion) is placed in a previously flamed 250 ml 3 neck, round-bottom flask and washed with hexane under a nitrogen atmosphere. A solution of dimethylformamide (10 ml) and benzene (20 ml) is added, followed by the dropwise addition of 2-benzyl-4-(2-fluorobenzyl)-1,2,3,4-tetrahydro-4-isoquinolinol (3.4 g) in benzene (30 ml) at room temperature. After refluxing for three days, toluene (20 ml) is added and reflux is continued for three additional days. An additional 0.25 g of 99% sodium hydride is added, and the mixture is refluxed overnight. The reaction mixture is cooled, poured into water and extracted with benzene. The benzene extract is washed with saturated sodium chloride solution and dried over anhydrous magnesium sulfate. Removal of the benzene affords a brown oil. The oil is dissolved in ether, filtered, and ethereal hydrogen chloride is added to give a tan powder. Recrystallization from isopropanol/methanol gives 1.9 g (53%) of product as a solid, mp 214°–216°.

ANALYSIS: Calculated for $C_{23}H_{21}NO \cdot HCl$: 75.91%C 6.11%H 3.85%N Found: 75.97%C 6.13%H 3.82%N

EXAMPLE 3

4-(2-Fluorobenzyl)-2-methyl-1,2,3,4-tetrahydro-4-isoquinolinol hydrochloride

To a suspension of magnesium shavings (3.96 g) and a crystal of iodine in anhydrous ether (50 ml) is added several milliliters of 2-fluorobenzyl chloride. After initiation of the reaction with a hot air gun, the remainder of the 2-fluorobenzyl chloride for a total of 27.2 g is added dropwise as a solution in ether (50 ml). After the addition is complete, the reaction mixture is refluxed for 2 hours. A solution of 2-methyl-2,3-dihydro-4(1H)-isoquinolone (24.2 g) in ether (100 ml) is added dropwise at room temperature. The granular precipitate which forms is stirred at room temperature for one hour, filtered and washed with ether. The solid is hydrolyzed by stirring at room temperature for one hour with an ammonium chloride solution, followed by ether extraction. The ether extract is washed with saturated sodium chloride solution and dried over anhydrous magnesium sulfate. Removal of the ether yields 28.6 g of an oil. A portion of the oil (5 g) is dissolved in ether, filtered, and ethereal hydrogen chloride is added to give product as a white powder (5.5 g, 97%), mp 105°.

ANALYSIS: Calculated for $C_{17}H_{18}FNO \cdot HCl$: 66.34%C 6.22%H 4.55%N Found: 66.23%C 6.32%H 4.51%N

EXAMPLE 4

2'-Methylspiro[benzofuran-2(3H),4'(2'H)-isoquinoline]-hydrochloride

Sodium hydride (2.98 g 50% oil dispersion) is placed in a previously flamed 500 ml 3 neck round-bottom flask and washed with hexane under a nitrogen atmosphere. Benzene (100 ml) is added, followed by the dropwise addition of 4-(2-fluorobenzyl)-2-methyl-1,2,3,4-tetrahydro-4-isoquinolinol (15 g) in benzene (100 ml). Dimethylformamide (30 ml) is added and the mixture is heated under reflux. Sodium hydride (99%, 1.5 g) is added, followed by toluene (100 ml) and dimethylformamide (30 ml) and the mixture is heated under reflux for 48 hours. The reaction mixture is cooled, poured into water and extracted with ether. The ether extract is washed with saturated sodium chloride and dried over anhydrous magnesium sulfate. Removal of the ether yields an oil. The oil is dissolved in ether, filtered and ethereal hydrogen chloride is added to give crystals. Recrystallization from isopropanol/ether yields 6.2 g (39%) of product as a solid, mp 214°-215°.

ANALYSIS: Calculated for $C_{17}H_{17}NO.HCl$: 70.95%C 6.30%H 4.87%N Found: 70.65%C 6.46%H 4.76%N

EXAMPLE 5

N-Phenoxycarbonylspiro[benzofuran-2(3H),4'(2'H)-isoquinoline]

To a previously flamed 2000 ml round-bottom flask is added N-methylspiro[benzofuran-2(3H),4'(2'H)-isoquinoline] (32.5 g) in dichloromethane (700 ml). To this is added phenylchloroformate (20 ml). The mixture is stirred overnight. Removal of the solvent yields an oil. Trituration with n-propanol followed by recrystallization of 4.0 g of the solid so formed from ethyl acetate yields 2.6 g (69.7%) of product, mp 128°.

ANALYSIS: Calculated for $C_{23}H_{19}NO_3$: 77.29%C 5.36%H 3.92%N Found: 77.12%C 5.45%H 3.78%N

EXAMPLE 6

2'-Ethoxycarbonylspiro[benzofuran-2(3H),4'(2'H)-isoquinoline]

A solution of 2'-methylspiro[benzofuran-2(3H),4'(2'H)-isoquinoline] (26.1 g) and ethyl chloroformate (12.4 g) is heated under reflux in benzene (275 ml) overnight. The reaction mixture is washed with water (3x), saturated sodium chloride solution and dried over anhydrous magnesium sulfate. After filtering, the solvent is removed to yield 24 g (76%) of product as a solid, mp 65°-75°. A sample is thrice recrystallized from hexane to yield the product, mp 89°-90°.

ANALYSIS: Calculated FOR $C_{19}H_{19}NO_3$: 73.76%C 6.19%H 4.53%N Found: 73.63%C 6.35%H 4.51%N

EXAMPLE 7

2'-Cyanospiro[benzofuran-2(3H),4'(2'H)-isoquinoline]

A solution of 2'-methylspiro[benzofuran-2(3H),4'(2H)-isoquinoline] (5.5 g) in chloroform (50 ml) is dropped into a refluxing mixture of potassium carbonate (15 g) and cyanogen bromide (2.6 g) in chloroform (60 ml). The reaction mixture is stirred at reflux for five hours. After filtration, the chloroform solution is washed with water, saturated sodium chloride solution and dried over anhydrous magnesium sulfate. Removal of solvent in vacuo yields an oil which crystallizes upon trituration with hexane to yield product as a solid (5.0 g, 86%), mp 65°-76°. An analytical sample is prepared by recrystallization (twice) from absolute ethanol to yield white needles, mp 102°-103.5°.

ANALYSIS: Calculated for $C_{17}H_{14}N_2O$: 77.84%C 5.38%H 10.68%N Found: 78.08%C 5.42%H 10.70%N

EXAMPLE 8

2'-Carboxamidoximespiro[benzofuran-2(3H),4'(2'H)-isoquinoline] hydrochloride

To dimethylformamide (25 ml) is added 2'-cyanospiro[benzofuran-2(3H),4'(2'H)-isoquinoline] (9.2 g), hydroxylamine hydrocholoride (4.3 g) and sodium carbonate (12.7 g). After stirring at 105° for two hours, the mixture is cooled, concentrated in vacuo to yield an oil which is stirred with water and extracted with ether. The combined ether extracts are washed with water (2x), saturated sodium chloride solution and dried over anhydrous magnesium sulfate. After filtering, the solvent is evaporated to give an oil which is dissolved in ether and converted to the hydrochloride salt (2.7 g, 27%). The salt is twice recrystallized from ethyl acetate/methanol to yield product as a solid, mp 184°-185° (dec.)

ANALYSIS: Calculated for $C_{17}H_{17}N_3O_2.HCl$: 61.53%C 5.47%H 12.67%N Found: 61.33%C 5.54%H 12.66%N

EXAMPLE 9

4-(2-Fluorobenzyl)-6,7-dimethoxy-2-methyl-1,2,3,4-tetrahydro-4-isoquinolinol

To a suspension of magnesium shavings (1.5 g) and a few crystals of iodine in anhydrous ether (50 ml) is added dropwise 2-fluorobenzyl chloride (8.7 g) in anhydrous ether (20 ml). After the addition is complete, the reaction mixture is refluxed for 30 minutes. A solution of 6,7-dimethoxy-2-methyl-2,3-dihydro-4(1H)-isoquinolone (8.8 g) in tetrahydrofuran (100 ml) is added dropwise. After the addition is completed, the reaction mixture is heated under reflux for three hours. The reaction mixture is stirred in 500 ml saturated ammonium chloride solution for one hour and extracted with ether. The combined ether extracts are washed with water (2x), saturated sodium chloride solution and dried over anhydrous magnesium sulfate. After filtering, the solvent is removed to yield a solid, which upon trituration with ether, yields 9.8 g (74%) of product as a solid, mp 59°-64°. A sample is twice crystallized from ether to yield a solid, mp 117°-118°.

ANALYSIS: Calculated for $C_{19}H_{22}FNO_3$: 68.86%C 6.69%H 4.23%N Found: 68.63%C 6.55%H 4.42%N

EXAMPLE 10

6',7'-Dimethoxy-2'-methylspiro[benzofuran-2(3H),4'(2'H)-isoquinoline] hydrochloride A solution of 4-(2-fluorobenzyl)-6,7-dimethoxy-2-methyl-1,2,3,4-tetrahydro-4-isoquinolinol (17.4 g) in toluene (50 ml) and dimethylformamide (25 ml) is added dropwise to a suspension of sodium hydride (50% oil dispersion, 5.1 g), previously washed with hexane, in toluene (180 ml) and dimethylformamide (40 ml). The reaction mixture is heated under reflux for 1.5 hours. The reaction mixture, after cooling, is stirred in water (1:1) and extracted with chloroform. The combined organic extracts are washed with water, saturated sodium chloride solution and dried over anhydrous magnesium sulfate. After filtering, removal of solvent yields an oil which is dissolved in ether and converted to the hydrochloride salt (12.2 g, 66%), mp 130°-135° (dec.). A sample is twice recrystallized from ethyl acetate/methanol to yield product as a white solid, mp 184°-185° (dec.).

ANALYSIS: Calculated for $C_{19}H_{21}NO_3 \cdot HCl$: 65.60%C 6.39%H 4.03%N Found: 65.51%C 6.61%H 3.96%N

EXAMPLE 11

6',7'-Dimethoxy-2'-ethoxycarbonylspiro[benzofuran-2(3H),4'(2'H)-isoquinoline]

A mixture of 6',7'-dimethoxy-2'-methylspiro[benzofuran-2(3H),4'(2'H)-isoquinoline] (20.6 g), ethyl chloroformate (10.9 g) and potassium carbonate (20 g) in dry benzene (400 ml) is heated under reflux overnight. The reaction mixture is cooled and stirred with water (200 ml) for 15 minutes. The organic phase is washed with water, diluted hydrochloric acid, saturated sodium chloride solution and dried over anhydrous magnesium sulfate. After filtering, the solvent is removed to yield 14.9 g of product as an oil. An analytical sample is obtained by passing 2.0 g of the oil through a silical gel dry column using ethyl acetate as the eluent and chloroform as the extractor. Removal of the solvent yields 1.8 g of an oil which crystallizes in the cold over petroleum ether, yielding a solid, mp, 72°-76°. The solid is recrystallized from hexane to yield white crystals, mp 75°-76°.

ANALYSIS: Calculated for $C_{21}H_{23}NO_5$: 68.27%C 6.28%H 3.79%N Found: 68.03%C 6.31%H 3.73%N

EXAMPLE 12

6',7'-Dimethoxyspiro[benzofuran-2(3H),4'(2'H)-isoquinoline] maleate

A mixture of 6',7'-dimethoxy-2'-ethoxycarbonylspiro[benzofuran-2(3H),4'(2'H)-isoquinoline] (4.2 g), potassium hydroxide (7.0 g) and water (7.0 ml) in n-propanol (150 ml) is heated under reflux for four hours. Removal of the solvent under reduced pressure yields an oil which is stirred in water (300 ml) and then extracted with chloroform. The combined organic phases are washed with water, saturated sodium chloride solution and dried over anhydrous magnesium sulfate. After filtering, the solvent is removed to yield 3.1 g (81%) of product as an oil which is dissolved in ether and converted to the maleate salt (1.9 g), mp 165°-167°. The material is twice recrystallized from ethyl acetate/methanol to yield a white solid (1.4 g), mp 180°-181° (dec.)

ANALYSIS: Calculated for $C_{18}H_{19}NO_3 \cdot C_4H_4O_4$: 63.91%C 5.61%H 3.39%N Found: 63.94%C 5.66%N 3.30%N

EXAMPLE 13

6',7'-Dimethoxy-2'-propylspiro[benzofuran-2(3H),4'(2'H)-isoquinoline] hydrochloride To a cooled solution of 6',7'-dimethoxyspiro[benzofuran-2(3H),4'(2'H)-isoquinoline] (5.3 g) and triethylamine (2.0 g) in dichloromethane (50 ml) is slowly added dropwise propionyl chloride (1.8 g) in dichloromethane. After stirring for two hours at ambient temperature, the reaction mixture is washed with water (2x), saturated sodium chloride solution and dried over anhydrous magnesium sulfate. After filtering, the solvent is removed to yield a solid (6.7 g) which is dissolved in tetrahydrofuran (50 ml) and slowly added dropwise to a refluxing suspension of lithium aluminum hydride (1.4 g) in tetrahydrofuran (100 ml). After refluxing for six hours, the reaction mixture is cooled and quenched by dropwise addition of saturated ammonium chloride solution (100 ml). The mixture is filtered, diluted with ether, washed with water (2x), saturated sodium chloride solution and dried over anhydrous magnesium sulfate. After filtering, the solvent is removed to yield an oil which is dissolved in ether and converted to the hydrochloride salt (5.2 g, 76%). The salt is twice recrystallized from ethyl acetate/methanol to yield a solid, mp 171°-172° (dec.).

ANALYSIS: Calculated for $C_{21}H_{25}NO_3 \cdot HCl$: 67.10%C 6.97%H 3.73%N Found: 67.26%C 6.96%H 3.71%N

EXAMPLE 14

6',7'-Dimethoxy-2'-(3-N,N-dimethylaminopropyl)-spiro[benzofuran-2-(3H),4'(2'H)-isoquinoline] dihydrochloride A mixture of 6',7'-dimethoxyspiro[benzofuran-2(3H),4'(2'H)isoquinoline] (5.0 g), 3-dimethylaminopropyl chloride (4.1 g) potassium carbonate (8.0 g) and a few crystals of potassium iodide in n-butanol (100 ml) is heated under reflux for four hours. Removal of the solvent yields an oil which is stirred in water and extracted with ether. The combined organic phases are washed with water (2 x), saturated sodium chloride solution and dried over anhydrous magnesium sulfate. After filtering, the solvent is removed to yield an oil which is dissolved in ether and converted to the product dihydrochloride salt (4.3 g, 56%). The salt is twice crystallized from ethyl acetate/methanol to yield the analytical sample as a white solid, mp 200°-202° (dec.).

ANALYSIS: Calculated for $C_{23}H_{30}N_2O_3 \cdot 2HCl$: 60.65%C 7.08%H 6.15%N Found: 60.38%C 7.18%H 6.05%N

EXAMPLE 15

2'-(2-N,N-Diethylaminoethyl)-6',7'-dimethoxyspiro[benzofuran-2(3H),4'(2'H)-isoquinoline] dioxalate A mixture of 6',7'-dimethoxyspiro[benzofuran-2(3H),4'(2'H)-isoquinoline] (4.6 g), 2-diethylaminoethyl chloride (4.2 g), potassium carbonate (8.0 g) and a few crystals potassium iodide in n-butanol (100 ml) is heated under reflux for four hours. Removal of the solvent yields an oil which is stirred in water and extracted with ether. The combined organic phases are washed with water (2X), saturated sodium chloride solution and dried over anhydrous magnesium sulfate. After filtering, the solvent is removed to yield an oil which is dissolved in ether and converted to the product dioxalate salt (6.7 g, 78%). The salt is twice recrystallized from ethyl acetate/methanol to yield the analytical sample as a white solid, mp 175°-177° (dec.).

ANALYSIS: Calculated for $C_{24}H_{32}N_2O_3 \cdot 2(CO_2H)_2$: 58.32%C 6.29%H 4.86%N Found: 57.87%C 6.30%H 4.78%N

EXAMPLE 16

6',7'-Dimethoxy-2'-[N'-methyl-N-(3-dimethylaminopropyl)]amidinospiro[benzofuran-2(3H),4'(2'H)-isoquinoline] dinitrate To a stirred suspension of 6',7'-dimethoxy-2'-(N,S-dimethylthiocarbamyl)spiro[benzofuran-2(3H),4'(2'H)-isoquinoline] hydroiodide (8.8 g) in absolute ethanol (100 ml) was slowly dropped 3-dimethylaminopropylamine (1.9 g) in ethanol (20 ml). The reaction mixture is heated under reflux for two hours. After cooling, the reaction mixture is concentrated in vacuo to yield, after trituration with ether, a yellow solid (9.4 g). The solid is dissolved in chloroform (75 ml), ethanol (100 ml), water (60 ml) and 3 N nitric acid (25 ml) and silver nitrate (9 g) is added slowly. After collecting the precipitated silver iodide, the mixture is extracted with chloroform, dried and concentrated in vacuo to yield, after trituration with ethyl acetate, product as a solid (6.9 g, 72%). The solid is twice recrystallized from ethyl acetate/methanol to yield the analytical sample as white needles mp 148°–150° (dec.).

ANALYSIS: Calculated for $C_{25}H_{34}N_4O_3.2HNO_3$: 53.18%C 6.43%H 14.89%N Found: 52.95%C 6.21%H 14.72%N By employing 2-dimethylaminoethylamine in the process of Example 16, 6′7′-dimethoxy-2′-[N′-methyl-N-2-(dimethylaminoethyl]amidino spiro[benzofuran-2(3H),4′(2′H)isoquinoline] may be prepared.

EXAMPLE 17

4-(4-Chloro-2-fluorobenzyl)-2-methyl-1,2,3,4-tetrahydro-4-isoquinolinol

To a suspension of magnesium shavings (15.7 g) and a few crystals of iodine in anhydrous ether (200 ml) is slowly dropped 4-chloro-2-fluorobenzylbromide (146.0 g) in anhydrous ether (200 ml) at such a rate so as to maintain the ether reflux. After the addition is complete, the reaction mixture is heated under reflux for two hours. A solution of 2-methyl-2,3-dihydro-4(1H)-isoquinolone (70.2 g) in anhydrous ether (200 ml) is slowly added dropwise. After the addition is complete, the reaction mixture is heated under reflux for three hours. The reaction mixture, after cooling, is stirred in 1.5 l. saturated ammonium chloride and extracted with ether. The combined ether extracts are washed with water (2x), saturated sodium chloride solution and dried over anhydrous magnesium sulfate. After filtering, the solvent is removed to yield a solid, which upon trituration with petroleum ether, yields the product (109.5 g, 82%), mp 113°–116°. An analytical sample is recrystallized from anhydrous ether to yield needles, mp 116°–117°.

ANALYSIS: Calculated for $C_{17}H_{17}ClFNO$: 66.77%C 5.60%H 4.58%N Found: 66.81%C 5.55%H 4.56%N

EXAMPLE 18

6-Chloro-2′-methylspiro[benzofuran-2(3H),4′(2′H)-isoquinoline] hydrochloride

A solution of 4-(4-chloro-2-fluorobenzyl)-2-methyl-1,2,3,4-tetrahydro-4-isoquinolinol (10.0 g) in toluene (65 ml) and dimethylformamide (10 ml) is added dropwise to a suspension of sodium hydride (50%, 3.2 g), previously washed with hexane, in toluene (65 ml). After the addition is complete, the mixture is brought to reflux and dimethylformamide (35 ml) is slowly added dropwise. The reaction mixture is heated under reflux for four hours. Removal of the solvents yields an oil which is stirred in water (500 ml) and extracted with chloroform. The combined organic extracts are washed with water, saturated sodium chloride solution and dried over anhydrous magnesium sulfate. After filtering, removal of the solvent yields an oil which is dissolved in ether and converted to the product hydrochloride salt. The salt is recrystallized from ethyl acetate/methanol to yield the product as a white solid (6.8 g, 60%), mp 196°–199°. An analytical sample is twice recrystallized to yield a white solid, mp 200.5°–202° (dec.).

ANALYSIS: Calculated for $C_{17}H_{16}ClNO.HCl$: 63.36%C 5.32%H 4.35%N Found: 63.20%C 5.39%H 4.30%N

EXAMPLE 19

6-Chloro-2′-phenoxycarbonylspiro[benzofuran-2(3H),4′(2′H)-isoquinoline]

To an ice cold solution of 6-chloro-2′-methylspiro[benzofuran-2(3H),4′(2′H)-isoquinoline] (5.0 g) in dichloromethane (150 ml) is slowly added dropwise phenyl chloroformate (3.7 g) in dichloromethane (20 ml). The mixture is stirred at ambient temperature overnight. Removal of the solvent in vacuo yields an orange oil which solidifies upon trituration with hexane. An analytical sample is twice recrystallized from hexane to yield product as a solid (6.6 g, 99%), mp 138°–140°.

ANALYSIS: Calculated for $C_{23}H_{18}ClNO_3$: 70.50%C 4.63%H 3.58%N Found: 70.56%C 4.72%H 3.35%N

EXAMPLE 20

6-Chlorospiro[benzofuran-2(3H),4′(2′H)-isoquinoline] hydrochloride

A mixture of 6-chloro-2′-phenoxycarbonylspiro[benzofuran-2(3H),4′(2′H)-isoquinoline] (25.0 g), potassium hydroxide (25 g) and water (25 ml) in n-propanol (250 ml) is heated under reflux for four hours. Removal of the solvent under reduced pressure yields a solid which is stirred with water (500 ml) and extracted with ether. The combined ether extract is washed with 3 N hydrochloric acid and basified with saturated sodium carbonate solution. The material which separates is extracted with ether, washed with saturated sodium chloride solution and dried over anhydrous magnesium sulfate. After filtering, the solvent is removed to yield product as a solid (13.5 g, 78%). A 4.0 g portion of the solid is dissolved in ether and converted to the product hydrochloride salt (4.3 g). An analytical sample is twice recrystallized from ethyl acetate/methanol, mp 238°–239° (dec).

ANALYSIS: Calculated for $C_{16}H_{14}ClNO.HCl$: 62.35%C 4.91%H 4.55%N Found: 62.33%C 4.93%H 4.47%N

EXAMPLE 21

6-Chloro-2′-ethyloxalylspiro[benzofuran-2(3H),4′(2′H)isoquinoline]

To a stirred mixture of 6-chlorospiro[benzofuran-2(3H),4′(2′H)-isoquinoline] (5.0 g) and sodium bicarbonate (10 g) in chloroform 50 ml) is slowly added dropwise ethyl oxalyl chloride (3.8 g) in chloroform (15 ml). The reaction mixture is heated under reflux for 3.5 hours. After cooling, the reaction mixture is filtered and concentrated in vacuo to an oil which, upon trituration with hexanes at −78°, yields the product as a white solid (6.2 g, 93%). An analytical sample is recrystalled from hexane to yield needles, mp 127°–128°.

ANALYSIS: Calculated for $C_{20}H_{18}ClNO_4$: 64.60%C 4.88%H 3.77%N Found: 64.44%C 4.92%H 3.59%N

EXAMPLE 22

Spiro[benzofuran-2(3H),4′(2′H)-isoquinoline] hydrochloride

A solution of N-phenoxycarbonylspiro[benzofuran-2(3H),4′(2′H)-isoquinoline] (13.7 g) and potassium hydroxide (20 g) in n-propanol (250 ml) and water (6 ml) is heated under reflux for 24 hours. Evaporation of solvent yields an oil. Water (300 ml) is added to the oil. The oil which separates is extracted with chloroform. The organic layer is collected, washed with water, saturated sodium chloride solution and dried over anhydrous magnesium sulfate. Removal of the solvent yields a solid, which is converted to the hydrochloride salt. Recrystallization from isopropanol/methanol yields product (5.5 g, 52%) mp, 229°–230°.

ANALYSIS: Calculated for $C_{16}H_{15}NO.HCl$: 70.20%C 5.89%H 5.12%N Found: 69.93%C 5.90%H 5.04%N

EXAMPLE 23

2′-(Cyclopropylcarbonyl)spiro[benzofuran-2(3H),4′(2′H)-isoquinoline]

To a cooled solution of spiro[benzofuran-2(3H),4′(2′H)-isoquinoline] (6.3 g) and triethylamine (3.2 g) in dichloromethane (35 ml) is added dropwise cyclopropylcarbonyl chloride (3.3 g) in dichloromethane (20 ml). The reaction mixture is washed with water (2x), saturated sodium chloride solution and dried over anhydrous magnesium sulfate. Removal of the solvent yields an oil (8.2 g). Trituration of 3.0 g with hexane yields a solid (2.0 g), which is recrystallized from hexane to yield product as crystals (1.6 g, 54%), mp 124°–125°.

ANALYSIS: Calculated for $C_{20}H_{19}NO_2$: 78.66%C 6.27%H 4.59%N Found: 78.46%C 6.45%H 4.58%N

EXAMPLE 24

2′-(Cyclopropylmethyl)-spiro[benzofuran-2(3H),4′(2′H)-isoquinoline] hydrochloride To a previously flamed 500 ml four-neck round bottom flask is added lithium aluminum hydride (1.3 g) and dry tetrahydrofuran (100 ml). To the stirred refluxing suspension is added dropwise 2′-cyclopropylcarbonyl-spiro[benzofuran-2(3H),4′(2′H)-isoquinoline] (5.2 g) in dry tetrahydrofuran (35 ml). After refluxing for 24 hours, the reaction mixture is cooled and quenched by the dropwise addition of 100 ml saturated ammonium chloride solution. The reaction mixture is filtered, diluted with ether, and the organic layer is washed with water (2x), saturated sodium chloride solution and dried over anhydrous magnesium sulfate. Removal of the solvent yields an oil, which is dissolved in ether and converted to the hydrochloride salt. Recrystallization from ethyl acetate/methanol yields product (3.2 g, 58%), mp 240°–242°.

ANALYSIS: Calculated for $C_{20}H_{21}NO.HCl$: 73.27%C 6.76%H 4.27%N Found: 73.24%C 6.85%H 4.40%N

EXAMPLE 25

2′-Propionylspiro[benzofuran-2(3H),4′(2′H)-isoquinoline]

To a cooled solution of spiro[benzofuran-2(3H),4′(2′H)-isoquinoline] (6.0 g) and triethylamine (3.1 g) in dichloromethane (35 ml) is added dropwise propionyl chloride (2.8 g) in dichloromethane (20 ml). After stirring for 24 hours, the reaction mixture is washed with water (2x), saturated sodium chloride solution and dried over anhydrous magnesium sulfate. The solution is filtered and the solvent removed to yield an oil (68 g). Trituration of 2.0 g of the oil with hexane yields a solid which is recrystallized from hexane to yield product (1.0 g, 50%), mp 97°–98°.

ANALYSIS: Calculated for $C_{19}H_{19}NO_2$: 77.79%C 6.53%H 4.78%N Found: 77.66%C 6.61%H 4.80%N

EXAMPLE 26

2′-(n-Propyl)spiro[benzofuran-2(3H),4′(2′H)-isoquinoline] hydrochloride

To a previously flamed 500 ml four-neck round bottom flask is added lithium aluminum hydride (1.2 g) and dry tetrahydrofuran (100 ml). To the stirred refluxing suspension is added dropwise 2′-propionylspiro[benzofuran-2(3H),4′(2′H)-isoquinoline] (4.8 g) in dry tetrahydrofuran (35 ml). After refluxing for 24 hours, the reaction mixture is cooled and quenched by the dropwise addition of saturated ammonium chloride solution (100 ml). The reaction mixture is filtered, diluted with ether, and the organic layer is washed with water (2x), saturated sodium chloride solution and dried over anhydrous magnesium sulfate. Removal of the solvent yields an oil, which is dissolved in ether and converted to the hydrochloride salt. Recrystallization from ethyl acetate/methanol yields the product as a white solid (2.9 g, 57%), mp 234°–235°.

ANALYSIS: Calculated for $C_{19}H_{21}NO.HCl$: 72.25%C 7.02%H 4.44%N Found: 72.03%C 6.98%H 4.57%N

EXAMPLE 27

2′-Acetylspiro[benzofuran-2(3H),4′(2′H)-isoquinoline]

To a cooled solution of spiro[benzofuran-2(3H),4′(2′H)-isoquinoline] (8.0 g) and triethylamine (4.1 g) in dichloromethane (35 ml) is added dropwise acetyl chloride (3.2 g) in dichloromethane (20 ml). After stirring at ambient temperature for 20 hours, the reaction mixture is washed with water (2x), saturated sodium chloride solution and dried over anhydrous magnesium sulfate. Removal of the solvent yields a solid (6.2 g), of which 2.5 g is recrystallized from ethyl acetate to yield 1.4 g (56%) of product as a powder, mp 141°–142°.

ANALYSIS: Calculated for $C_{18}H_{17}NO_2$: 77.39%C 6.13%H 5.02%N Found: 76.99%C 6.21%H 5.04%N

EXAMPLE 28

2′-Ethylspiro[benzofuran-2(3H),4′(2′H)-isoquinoline] hydrochloride

To a previously flamed 500 ml four-neck round bottom flask is added lithium aluminum hydride (1.0 g) and dry tetrahydrofuran (100 ml). To the refluxing suspension is added dropwise 2′-acetylspiro[benzofuran-2(3H),4′(2′H)-isoquinoline] (3.7 g) in dry tetrahydrofuran (35 ml). After refluxing for 24 hours, the reaction mixture is cooled and quenched by dropwise addition of 70 ml saturated ammonium chloride solution. The reaction mixture is filtered, diluted with ether, and the organic layer is washed with water (2x), saturated sodium chloride solution and dried over anhydrous magnesium sulfate. Removal of the solvent yields an oil, which is dissolved in ether and converted to the hydrochloride salt. Recrystallization from ethyl acetate/methanol yields 2.2 g (56%) of product as crystals, mp 220°–222°.

ANALYSIS: Calculated for $C_{18}H_{19}NO.HCl$: 71.63%C 6.68%H 4.64%N Found: 71.28%C 6.69%H 4.68%N

EXAMPLE 29

2'-(3,4,5-Trimethoxybenzoyl)spiro[benzofuran-2(3H),4'(2'H)-isoquinoline]

To a cold solution of spiro[benzofuran-2(3H),4'(2'H)-isoquinoline] (8.0 g) and triethylamine (4.0 g) in dry dichloromethane (100 ml) is added dropwise a solution of 3,4,5-trimethoxybenzoyl chloride (9.5 g) in dry dichloromethane (50 ml). After stirring at ambient temperature for 24 hours, the mixture is washed with water (2x), saturated sodium chloride solution and dried over anhydrous magnesium sulfate. After filtering, the solvent is evaporated to an oil, which solidifies upon trituration with hexanes. The solid is recrystallized twice from hexane/methanol to yield 10.0 g (66%) of product, mp 122° (dec.).

ANALYSIS: Calculated for $C_{26}H_{25}NO_5$: 72.37%C 5.85%H 3.25%N Found: 72.06%C 6.40%H 2.94%N

EXAMPLE 30

2'-(3,4,5-Trimethoxybenzyl)spiro[benzofuran-2(3H),4'(2'H)-isoquinoline] hydrochloride To a refluxing suspension of lithium aluminum hydride (1.9 g) in dry tetrahydrofuran, is added dropwise a solution of 2'-(3,4,5-trimethoxybenzoyl)spiro[benzofuran-2(3H),4'(2'H)-isoquinoline] (10.0 g) in dry tetrahydrofuran (50 ml). After refluxing at 70° for 20 hours, the mixture is cooled, quenched with 100 ml of saturated ammonium chloride solution, diluted with 200 ml of ether and filtered. The organic phase of the filtrate is washed with water (2x), saturated sodium chloride solution and dried over anhydrous magnesium sulfate. After filtering, the solvents are evaporated to give an oil, which is dissolved in ether and converted to the hydrochloride salt. The salt is recrystallized from ethyl acetate/methanol to yield 4.0 g (40%) of product, mp 210°.

ANALYSIS: Calculated for $C_{26}H_{27}NO_4.HCl$: 68.79%C 6.22%H 3.09%N Found: 68.72%C 6.29%H 3.18%N

EXAMPLE 31

2'-(2-Furoyl)spiro[benzofuran-2(3H),4'(2'H) isoquinoline]

To a solution of spiro[benzofuran-2(3H),4'(2'H)isoquinoline] (8.0 g) and triethylamine (4.1 g) in dichloromethane (40 ml), cooled in an ice-water bath, is added dropwise a solution of 2-furoyl chloride (5.3 g) in dichloromethane (20 ml). After the addition is complete, the reaction mixture is stirred at ambient temperature overnight. The reaction mixture is washed with water, saturated sodium chloride solution, dried over anhydrous magnesium sulfate and filtered. Evaporation of the filtrate provides produce (7.0 g, 63%) as an oil. Trituration of a portion of the oil with ether affords solid, mp ca. 110°.

EXAMPLE 31A

2'-(2-Furanylmethyl)spiro[benzofuran-2(3H),4'(2'H)-isoquinoline] hydrochloride

To a refluxing suspension of lithium aluminum hydride (1.6 g) in tetrahydrofuran (100 ml) is added dropwise a solution of 2'-(2-furoyl)spiro[benzofuran-2(3H),4'(2'H)-isoquinoline] (7.0 g) in dry tetrahydrofuran. After refluxing for 24 hours, the reaction mixture is cooled and quenched by the dropwise addition of saturated ammonium chloride solution (70 ml). The reaction mixture is filtered, diluted with ether and the organic layer is washed with water (2x), saturated sodium chloride solution and dried over anhydrous magnesium sulfate. Removal of solvent yields an oil which is dissolved in ether and converted to the hydrochloride salt. Recrystallization from acetone-ether yields 3.1 g (42%) of product as crystals, mp 93° (dec.).

ANALYSIS: Calculated for $C_{21}H_{19}NO_2.HCl$: 71.28%C 5.70%H 3.96%N Found: 71.11%C 6.25%H 4.28%N

EXAMPLE 32

2'-(3-Methyl-2-butenyl)spiro[benzofuran-2(3H),4'(2'H)-isoquinoline] hydrochloride To n-butanol (100 ml) is added spiro[benzofuran-2(3H),4'(2'H)-isoquinoline] (5.0 g), 1-bromo-3-methyl-2-butene (4.5 g), anhydrous potassium carbonate (20.0 g) and a few crystals of potassium iodide. After refluxing for 24 hours, the mixture is cooled, filtered and the solvent evaporated to an oil. The oil is stirred with water (300 ml) for 10 minutes and extracted with ether. The ether extract is washed with water (2x), saturated sodium chloride solution and dried over anhydrous magnesium sulfate. After filtering, the solvent is evaporated to an oil, which is dissolved in ether and converted to the product hydrochloride salt (4.0 g, 56%), mp 187°-93° (dec.). Recrystallization from ethyl acetate/methanol yields the analytical sample, mp 210° (dec.).

ANALYSIS: Calculated for $C_{21}H_{23}NO.HCl$: 73.77%C 7.08%H 4.10%N Found: 73.75%C 7.16%H 3.98%N

EXAMPLE 33

2'-(2-Propynyl)spiro[benzofuran-2(3H),4'(2'H)-isoquinoline] oxalate

A mixture of spiro[benzofuran-2(3H),4'(2'H)-isoquinoline (7.6 g) potassium carbonate (20 g), propargyl chloride (2.9 g) and a few crystals of potassium iodide is heated under reflux overnight. The reaction mixture is filtered and the solvent removed to yield an oil which is poured into water. The oil which separates is extracted with chloroform. The combined extracts are washed with water (2x), saturated sodium chloride solution and dried over anhydrous magnesium sulfate. Removal of the solvent yields an oil which is taken up in ether and converted to the oxalate salt. Recrystallization from ethyl acetate/methanol yields 1.73 g (15%) of product as a solid, mp 95°.

ANALYSIS: Calculated for $C_{19}H_{17}NO.(CO_2H)_2$: 69.03%C 5.24%H 3.83%N Found: 69.24%C 5.52%H 3.85%N

EXAMPLE 34

2'-(2-N,N-Diethylaminoethyl)spiro[benzofuran-2(3H),4'(2'H)-isoquinoline] dihydrochloride A solution of spiro[benzofuran-2(3H),4'(2'H)-isoquinoline] (7.0 g), diethylaminoethyl chloride (4.8 g,) potassium carbonate (20 g) and a few crystals of potassium iodide in n-butanol (100 ml) is heated under reflux overnight. The reaction mixture is filtered and the solvent is removed to yield an oil which is poured into water (600 ml) and extracted with ether. The ether layer is washed with water (2X), saturated sodium chloride solution and dried over anhydrous magnesium sulfate. Removal of the solvent yields an oil which is dissolved in ether and converted to the dihydrochloride salt. The salt is twice recrystallized from ethyl acetate/methanol to yield product as a white solid (4.40 g, 35%), mp 161° (dec.).

ANALYSIS: Calculated for $C_{22}H_{28}N_2O.2HCl$: 64.54%C 7.39%H 6.84%N Found: 64.44%C 7.45%H 6.77%N

EXAMPLE 35

2'-(3-N,N-Dimethylaminopropyl)spiro[benzofuran-2(3H),4'(2'H)-isoquinoline] dihydrochloride A mixture of spiro[benzofuran-2(3H),4'(2'H)-isoquinoline] (5.9 g), 3-dimethylaminopropyl chloride (4.5 g), potassium carbonate (20 g) and a few crystals of potassium iodide in n-butanol (100 ml) is heated under reflux overnight. The reaction mixture is filtered and the solvent is removed to yield an oil which is poured into water (500 ml) and extracted with ether. The combined organic phases are washed with water (2X), saturated sodium chloride solution and dried over anhydrous magnesium sulfate. Removal of the solvent yields an oil which is dissolved in ether and converted to the dihydrochloride salt. The salt is twice recrystallized from ethyl acetate/methanol to yield product as a white solid, mp 232°-234°.

ANALYSIS: Calculated for $C_{21}H_{26}N_2O.2HCl$: 63.79%C 7.14%H 7.09%N Found: 63.95%C 7.20%H 7.08%N

EXAMPLE 36

2'-(3-N-Methylaminopropyl)spiro[benzofuran-2(3H),4'(2'H)-isoquinoline] dihydrochloride To benzene (200 ml) is added 2'-(3-N,N-dimethylaminopropyl)spiro[benzofuran-2(3H),4'(2'H)-isoquinoline] (22.1 g), 2,2,2-trichloroethyl chloroformate (18.2 g) and potassium carbonate (10 g). After refluxing for 1.5 hours, the mixture is cooled and the solvent evaporated to an oil. The oil is dissolved in cold glacial acetic acid (125 ml) and to it is added zinc dust (85 g). The mixture becomes slightly warm and stirring is continued at ambient temperature for six hours. After filtering, the excess acetic acid is removed under reduced pressure to yield an oil which is dissolved in water (600 ml), basified with saturated sodium carbonate solution and extracted with ether. The combined organic phases are washed with water, saturated sodium chloride solution and dried over anhydrous magnesium sulfate. After filtering, the solvent is removed to yield an oil which is dissolved in ether and converted to the product dihydrochloride salt (8.0 g, 41%). The salt is twice recrystallized from ethyl acetate/methanol to yield the analytical sample as a white solid, mp 210°-213°.

ANALYSIS: Calculated for $C_{20}H_{24}N_2O.2HCl$: 62.99%C 6.87%H 7.35%N Found: 62.69%C 6.79%H 7.04%N

EXAMPLE 37

2'-Amidinospiro[benzofuran-2(3H),4'(2'H)-isoquinoline] nitrate

A solution of spiro[benzofuran-2(3H),4'(2'H)-isoquinoline] (4.2 g), 3,5-dimethylpyrazole carboxamidine nitrate (3.6 g) in 95% ethanol (80 ml) is heated under reflux for 7 hours. The mixture is evaporated to dryness in vacuo and the viscous residue is triturated with ether. After filtration, the precipitate is twice recrystallized from ethyl acetate/methanol to yield product (2.6 g, 42%) as a solid, mp 188°.

ANALYSIS: Calculated for $C_{17}H_{17}N_3O.HNO_3$: 59.64% 5.30%H 16.37%N Found: 59.69%C 5.32%H 16.49%N

EXAMPLE 38

2'-(N-Methylthiocarbamyl)spiro[benzofuran-2(3H),4'(2'H)-isoquinoline]

To a stirred solution of spiro[benzofuran-2(3H),4'(2'H)-isoquinoline] (5.0 g) in dry benzene (18 ml) is added methylisothiocyanate (3.1 g) in dry benzene (10 ml). After one hour, the product begins to separate. The mixture is stirred overnight and diluted with hexane (18 ml). The product is filtered, washed with hexane and dried to yield a solid. The solid is twice recrystallized from benzene to yield (3.0 g, 46%) as a solid, mp 165°-166°.

ANALYSIS: Calculated for $C_{18}H_{18}N_2OS$: 69.64%C 5.85%H 9.03%N Found: 69.74%C 5.83%H 8.79%N

EXAMPLE 39

2'-(N,S-Dimethylthiocarbamyl)spiro[benzofuran-2(3H),4'(2'H)-isoquinoline] hydroiodide A solution of 2'-(N-methylthiocarbamyl)spiro[benzofuran-2(3H),4'(2'H)-isoquinoline] (5.9 g) and iodomethane (4.1 g) in ethanol (45 ml) and methanol (100 ml) is heated under reflux overnight. Removal of the solvents yields a solid (8.1 g). The solid (1.0 g) is twice recrystallized from ethyl acetate/methanol to yield 0.6 g (60%) of product as crystals, mp 181°-182°.

ANALYSIS: Calculated for $C_{19}H_{20}N_2OS.HI$: 50.44%C 4.68%H 6.19%N Found: 50.34%C 4.68%H 6.08%N

EXAMPLE 40

2'-Aminospiro[benzofuran-2(3H),4'(2'H)-isoquinoline] hydrochloride

To a stirred solution of spiro[benzofuran-2(3H),4'(2'H)-isoquinoline] (7.0 g) in glacial acetic acid (30 ml) and water (12 ml) is added dropwise at 0°-5° under nitrogen a solution of sodium nitrite (4.1 g) in water (18 ml). After the addition is complete, the mixture is allowed to stir at room temperature for one hour. The mixture is diluted with water (60 ml), decanted and the residue is dissolved in dichloromethane, washed with water (3X), saturated sodium chloride solution and dried over anhydrous magnesium sulfate. The solution is filtered and concentrated to yield the intermediate nitroso compound as an oil (7.1 g). The oil is dissolved in glacial acetic acid (80 ml) and slowly added dropwise to a stirred solution of zinc dust (7.8 g) in 1:1 acetic acid-water (100 ml), under nitrogen, maintaining the temperature at 15°-20°. After the addition is complete, the mixture is allowed to stir at room temperature for one half hour. The mixture is then filtered and the zinc and inorganic salts are washed with 1 N hydrochloric acid. The filtrate is basified with 6 N sodium hydroxide solution and extracted with ether. The combined ether extracts are washed with water (2X) and dried over anhydrous magnesium sulfate. The solution is filtered and concentrated to an oil which is dissolved in ether and converted to the product hydrochloride salt (6.1 g, 80%). The salt is recrystallized four times from ethyl acetate/methanol to yield needles, mp 198°-199°.

ANALYSIS: Calculated for $C_{16}H_{16}N_2O\cdot HCl$: 66.54%C 5.93%H 9.70%N 12.28%Cl Found: 66.25%C 5.91%H 9.75%N 12.09%Cl

EXAMPLE 41

2'-Cyanomethylspiro[benzofuran-2(3H),4'(2'H)-isoquinoline]

To dry dimethylformamide is added spiro[benzofuran-2(3H),4'(2'H)-isoquinoline] (11.0 g), sodium bicarbonate (8.4 g) and chloroacetonitrile (6.8 g) and the mixture is heated to 70° for four hours. The dimethylformamide is evaporated to give an oil, which is stirred with water (300 ml) for 15 minutes and then extracted with ether/dichloromethane. The organic extract is washed with water (2X), saturated sodium chloride solution and then dried over anhydrous magnesium sulfate. After filtering, the solvents are evaporated to an oil which solidifies to the product (10.6 g, 83%), as an off-white solid upon trituration with petroleum ether/ether. For analysis, a sample is recrystallized twice from hexane/acetone to yield platelets.

ANALYSIS: Calculated for $C_{18}H_{16}N_2O$: 78.23%C 5.84%H 10.14%N Found: 78.16%C 5.85%H 10.17%N

EXAMPLE 42

2'-(2-Aminoethyl)spiro[benzofuran-2(3H),4'(2'H)-isoquinoline] dihydrochloride

To a stirred suspension of lithium aluminum hydride (5.3 g) in dry tetrahydrofuran (100 ml) at 0°, is added a solution of 2'-cyanomethylspiro[benzofuran-2(3H),4'(2'H)-isoquinoline] (9.5 g) in dry tetrahydrofuran (50 ml). The mixture is heated to reflux for three hours. The mixture is cooled with an ice-bath, diluted with dry ether (300 ml) and saturated ammonium chloride solution (60 ml) is added in small portions over a period of one hour. The organic layer is collected, washed with water (2X) and dried over anhydrous magnesium sulfate. After filtering, the solvents are evaporated to an oil (7.3 g). The oil (3.7 g) is dissolved in ether and converted to dihydrochloride salt. The material is recrystallized twice from methanol/acetone/ether to yield product (3.0 g, 67.5%) as a solid, mp 158° (dec).

ANALYSIS: Calculated for $C_{18}H_{20}N_2O\cdot 2HCl$: 61.19%C 6.28%H 7.93%N Found: 61.33%C 6.06%H 7.63%N

EXAMPLE 43

2'-(Guanidinoethyl)spiro[benzofuran-2(3H),4'(2'H)-isoquinoline] hemisulfate

To a solution of 2'-(2-aminoethyl)spiro[benzofuran-2(3H),4'(2'H)-isoquinoline] (3.6 g) in ethanol (15 ml) is added a solution of 2-methyl-2-thiopseudourea sulfate (1.8 g) in water (25 ml). After stirring at reflux (110°) for 20 hours, the mixture is cooled and diluted with ether (100 ml). The resultant precipitate is collected, washed with ether and dried to yield product (4.0 g, 83%). Recrystallization from methanol/ether yields the analytical sample as an off-white solid, mp 234°–239° (dec.).

ANALYSIS: Calculated for $C_{19}H_{22}N_4O\cdot 1/2\ H_2SO_4$: 61.44%C 6.24%H 15.08%N Found: 60.96%C 6.16%H 14.96%N

EXAMPLE 44

6-Chloro-2'-propionylspiro[benzofuran-2(3H),4'(2'H)-isoquinoline]

To a cooled solution of 6-chlorospiro[benzofuran-2(3H),4'(2'H)-isoquinoline] (6.0 g) and triethylamine (2.4 g) in dichloromethane (50 ml) is slowly added dropwise propionyl chloride (2.3 g) in dichloromethane (20 ml). The reaction mixture is stirred for 18 hours at ambient temperature, washed with water (2X), saturated sodium chloride solution and dried over anhydrous magnesium sulfate. After filtering, the solvent is removed to yield an oil which, upon trituration with hexane/ether, yields product as a white solid (6.6 g, 92%). An analytical sample is recrystallized from hexane to yield a white solid, mp 106°–107°.

ANALYSIS: Calculated for $C_{19}H_{18}ClNO_2$: 69.61%C 5.54%H 4.27%N Found: 69.57%C 5.61%H 4.68%N

EXAMPLE 45

6-Chloro-2'-propylspiro[benzofuran-2(3H),4'(2'H)-isoquinoline] hydrochloride

To a refluxing suspension of lithium aluminum hydride (1.4 g) in tetrahydrofuran (100 ml) is slowly dropped 6-chloro-2'-propionylspiro[benzofuran-2(3H),4'(2'H)-isoquinoline] (6.1 g) in tetrahydrofuran (50 ml). The reaction mixture is heated under reflux for four hours, cooled and quenched by the dropwise addition of saturated ammonium chloride solution (100 ml). The mixture is filtered, diluted with ether, washed with water (2X), saturated sodium chloride solution and dried over anhydrous magnesium sulfate. After filtering, the solvent is removed to yield an oil which is dissolved in ether and converted to the product hydrochloride salt (6.0 g, 90%). The salt is recrystallized from ethyl acetate/methanol to yield the analytical sample as a white solid, mp 227°–228° (dec.).

ANALYSIS: Calculated for $C_{19}H_{20}ClNO\cdot HCl$: 65.15%C 6.04%H 4.00%N Found: 65.37%C 6.06%H 3.98%N

EXAMPLE 46

6-Chloro-2'-(2-N,N-diethylaminoethyl)spiro[benzofuran-2(3H),4'(2'H)isoquinoline]dihydrochloride A mixture of 6-chlorospiro[benzofuran-2(3H),4'(2'H)-isoquinoline] (5.1 g), 2-diethylaminoethyl chloride (5.1 g), potassium carbonate (8.0 g) and a few crystals potassium iodide in n-butanol is heated under reflux for four hours. Removal of solvent yields an oil which is stirred in water (600 ml) and extracted with ether. The combined ether extracts are washed with water (2X), saturated sodium chloride solution and dried over anhydrous magnesium sulfate. After filtering, the solvent is removed to yield an oil which is dissolved in ether and converted to the dihydrochloride salt. The salt is twice recrystallized from ethyl acetate/methanol to yield the product as a white solid (5.7 g, 67.6%), mp 188°–190° (dec.).

ANALYSIS: Calculated for $C_{22}H_{27}ClN_2O\cdot 2HCl$: 59.53%C 6.59%H 6.31%N Found: 59.47%C 6.55%H 6.20%N

EXAMPLE 47

6-Chloro-2'-(3-piperidinopropylspiro[benzofuran-2(3H),4'(2'H)-isoquinoline] dihydrochloride A mixture of 6-chlorospiro[benzofuran-2(3H),4'(2'H)-isoquinoline] (6.5 g) 3-piperidinopropyl chloride (7.8 g) and potassium carbonate (10 g) in n-butanol (75 ml) is heated under reflux for 3.5 hours. Removal of solvent yields an oil which is stirred in water (500 ml) and then extracted with ether. The combined organic phases are washed with water (2X), saturated sodium chloride solution and dried over anhydrous magnesium sulfate. After filtering, the solvent is removed to yield an oil which is dissolved in ether and converted to the product dihydrochloride salt (8.7 g, 77%). The salt is twice recrystallized from ethyl acetate/methanol to yield the analytical sample as a white solid, mp 220°-222° (dec.).

ANALYSIS: Calculated for $C_{24}H_{29}ClN_2O \cdot 2HCl$: 61.34%C 6.65%H 5.96%N Found: 61.03%C 6.45%H 5.85%N By utilizing 3-pyrrolidinopropylchloride in the process of Example 47, 6-chloro-2'-(3-pyrrolidinopropyl)-spiro[benzofuran-2(3H),4'(2'H)isoquinoline] may be prepared.

EXAMPLE 48

6-Chloro-2'-N-methylthiocarbamyl)spiro[benzofuran-2(3H),4'(2'H)-isoquinoline]

To a stirred solution of 6-chlorospiro[benzofuran-2(3H),4'(2'H)-isoquinoline] (10.4 g) in dry benzene (50 ml) is slowly added dropwise methyl isothiocyanate (5.6 g) in benzene (25 ml). After one hour, the product begins to separate. The reaction mixture is stirred at ambient temperature overnight, diluted with hexane (60 ml), cooled and filtered to yield product as a solid (12.6 g, 96%). An analytical sample is recrystallized from benzene to yield a white solid, mp 195°-196°.

ANALYSIS: Calculated for $C_{18}H_{17}ClN_2OS$: 62.69%C 4.97%H 8.12%N Found: 63.05%C 4.88%H 8.09%N

EXAMPLE 49

6-Chloro-2'-(N,S-dimethylthiocarbamyl)spiro[benzofuran-2(3H),4'(2'H)isoquinoline] hydroiodide A solution of 6-chloro-2'-(N-methylthiocarbamyl)-spiro[benzofuran-2(3H),4'(2'H)-isoquinoline] (12.0 g) and iodomethane (7.4 g) in methanol (150 ml) and ethanol (100 ml) is heated under reflux for four hours. Removal of solvents in vacuo yields a solid which, upon trituration with ether, yields product as a solid (16.4 g, 99%). An analytical sample is recrystallized from ethyl acetate/methanol to yield a white solid, 181°-182° (dec.).

ANALYSIS: Calculated for $C_{19}H_{19}ClN_2OS \cdot HI$: 46.88%C 4.14%H 5.76%N Found: 46.76%C 4.01%H 5.57%N

EXAMPLE 50

6-Chloro-2'-[N'-methyl-N-(3-dimethylaminopropyl)-]amidinospiro[benzofuran-2(3H),4'(2'H)-isoquinoline hydroiodide To a stirring suspension of 6-chloro-2'-(N,S-dimethylthiocarbamyl)spiro[benzofuran-2(3H),4'(2'H)-isoquinoline] (8.0 g) in absolute ethanol (100 ml) is slowly added dropwise 3-dimethylaminopropylamine (1.9 g) in ethanol (20 ml). After cooling, the reaction mixture is concentrated in vacuo to yield a gummy solid which is recrystallized from ethyl acetate/methanol to yield product as a solid (6.9 g, 78%). The product is recrystallized from ethyl acetate/methanol to yield needles, mp 190°-191°.

ANALYSIS: Calculated for $C_{23}H_{29}ClN_4O \cdot HI$: 51.07%C 5.59%H 10.36%N Found: 50.88%C 5.56%H 10.23%N

EXAMPLE 51

6-Chloro-2'-(3-N,N-dimethylaminopropyl)spiro[benzofuran-2(3H),4'(2'H)-isoquinoline] dihydrochloride A mixture of 6-chlorospiro[benzofuran-2(3H),4'(2'H)-isoquinoline] (16.0 g), 3-dimethylaminopropyl chloride (14.3 g) and potassium carbonate (25 g) in n-butanol (300 ml) is heated under reflux for 3.5 hours. Removal of solvent yields an oil which is stirred in water (600 ml) and extracted with ether. The combined organic phases are washed with water (2X), saturated sodium chloride solution and dried over anhydrous magnesium sulfate. After filtering, the solvent is removed to yield an oil (5.0 g), which is dissolved in ether and converted to the dihydrochloride salt (5.8 g, 75%). The salt is twice recrystallized from ethyl acetate/methanol to yield the analytical sample, mp 234°-235°.

ANALYSIS: Calculated for $C_{21}H_{25}ClN_2O \cdot 2HCl$: 58.68%C 6.33%H 6.52%N Found: 58.76%C 6.34%H 6.41%N

EXAMPLE 52

6-Chloro-2'-(3-N,N-dimethylamino-2-methylpropyl)-spiro[benzofuran-2(3H),4'(2'H)-isoquinoline] dioxalate A mixture of 6-chlorospiro[benzofuran-2(3H),4'(2'H)-isoquinoline] (5.0 g), 3-dimethylamino-2-methylpropyl chloride (5.0 g) and potassium carbonate (7.0 g) in n-butanol (100 ml) is heated under reflux for 3.5 hours. Removal of solvent yields an oil which is stirred in water (400 ml) and extracted with ether. The combined organic phases are washed with water (2X), saturated sodium chloride solution and dried over anhydrous magnesium sulfate. After filtering, the solvent is removed to yield an oil which is dissolved in ether and converted to the product dioxalate salt (7.4 g, 75%). The salt is twice recrystallized from ethyl acetate/methanol to yield the analytical sample as a white solid, mp 190°-191°.

ANALYSIS: Calculated for $C_{22}H_{27}ClN_2O \cdot 2(CO_2H)_2$: 56.67%C 5.67%H 5.09%N Found: 56.80%C 5.90%H 4.62%N REACTION SCHEME I
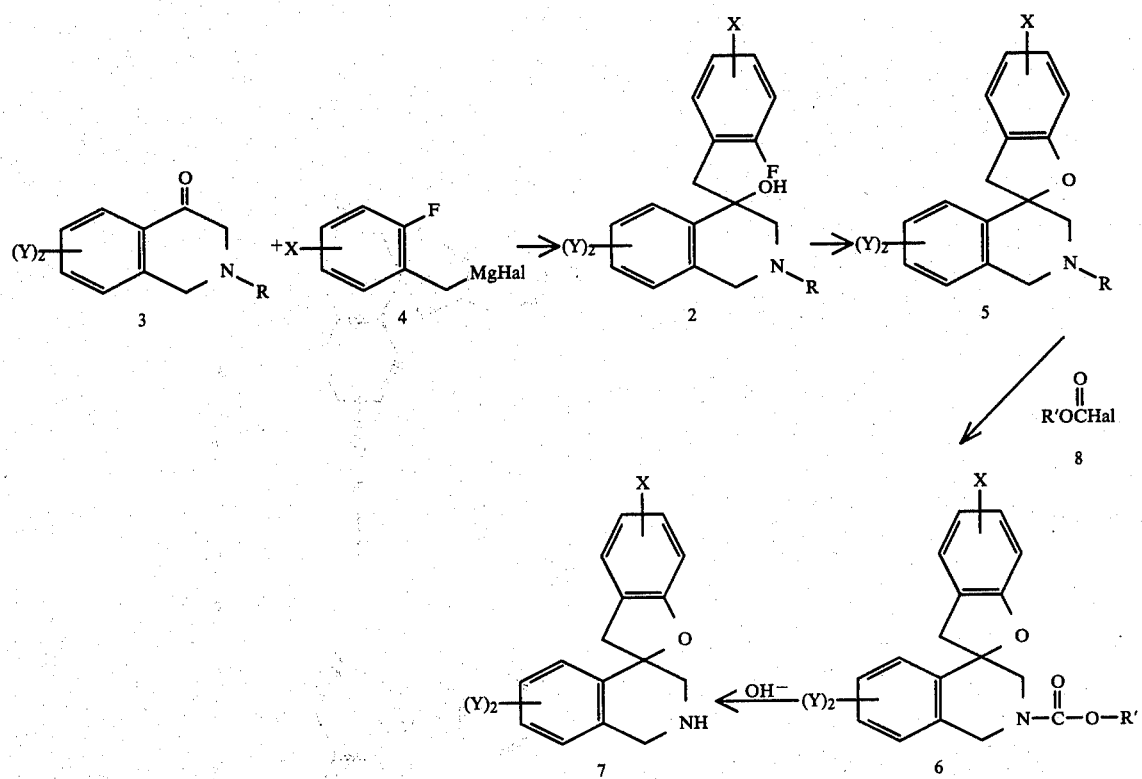
Wherein R is loweralkyl or benzyl; R¹ is loweralkyl or phenyl; Hal is chloro or bromo; X is hydrogen or halogen and Y is hydrogen or methoxy.

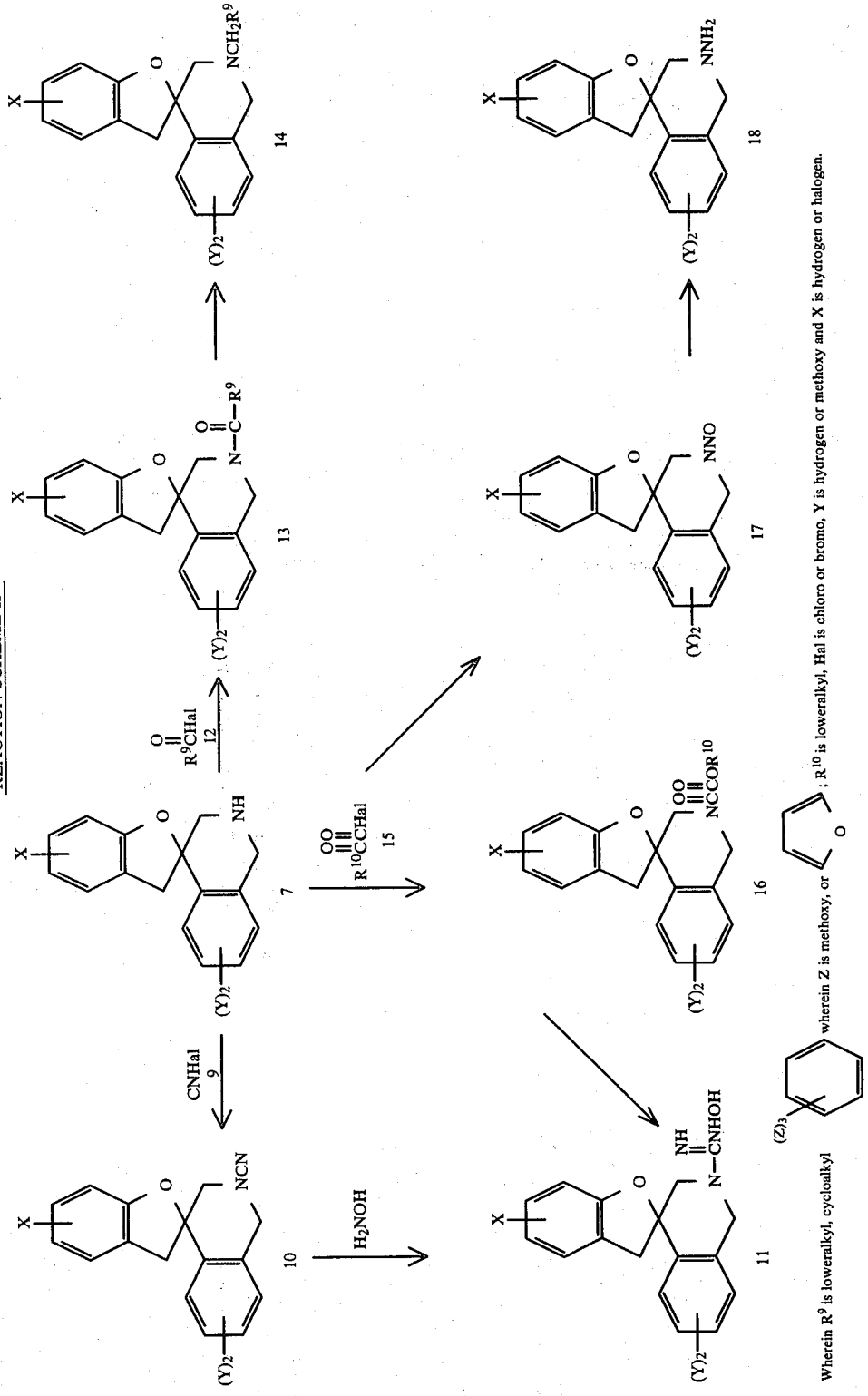
REACTION SCHEME II

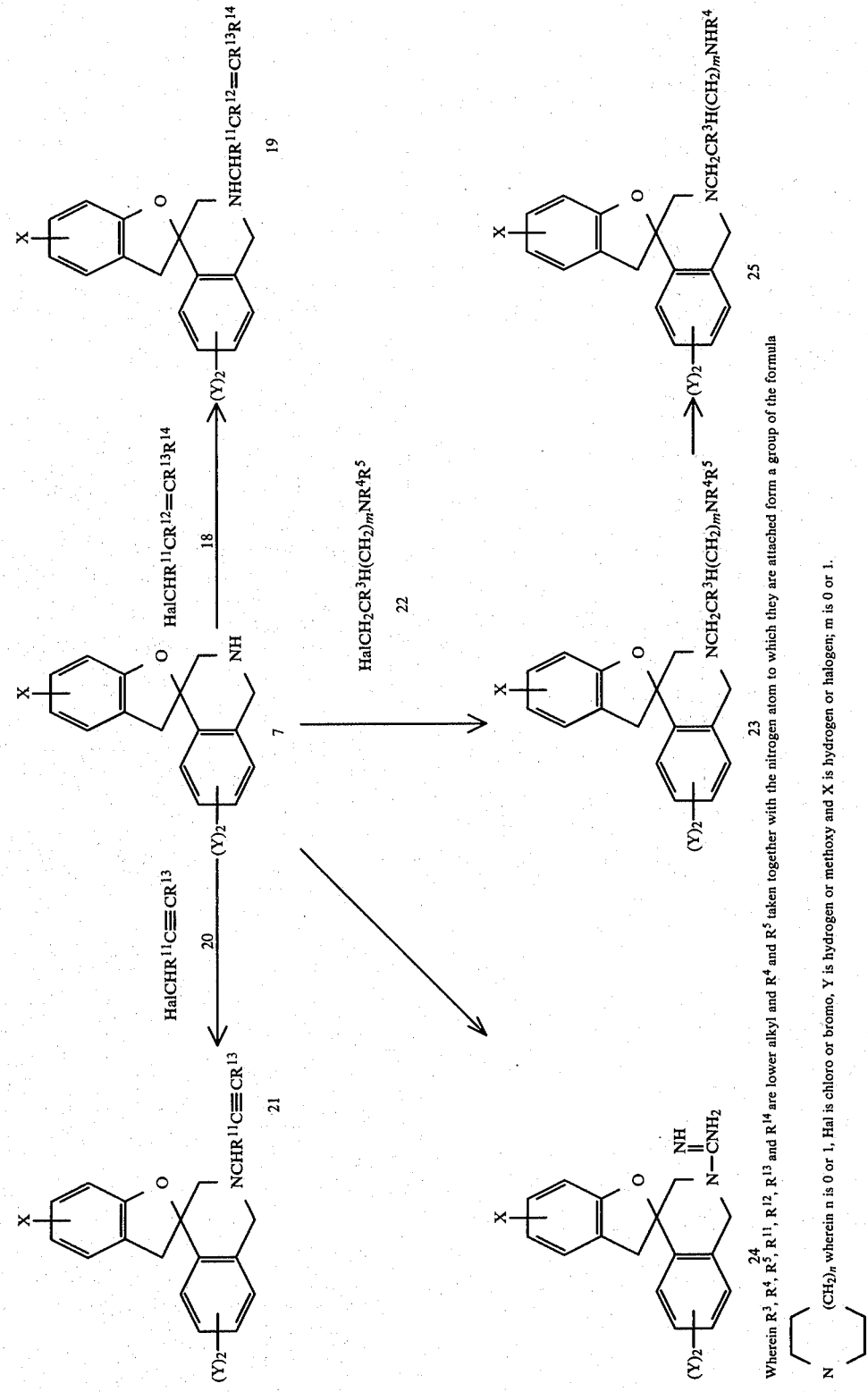

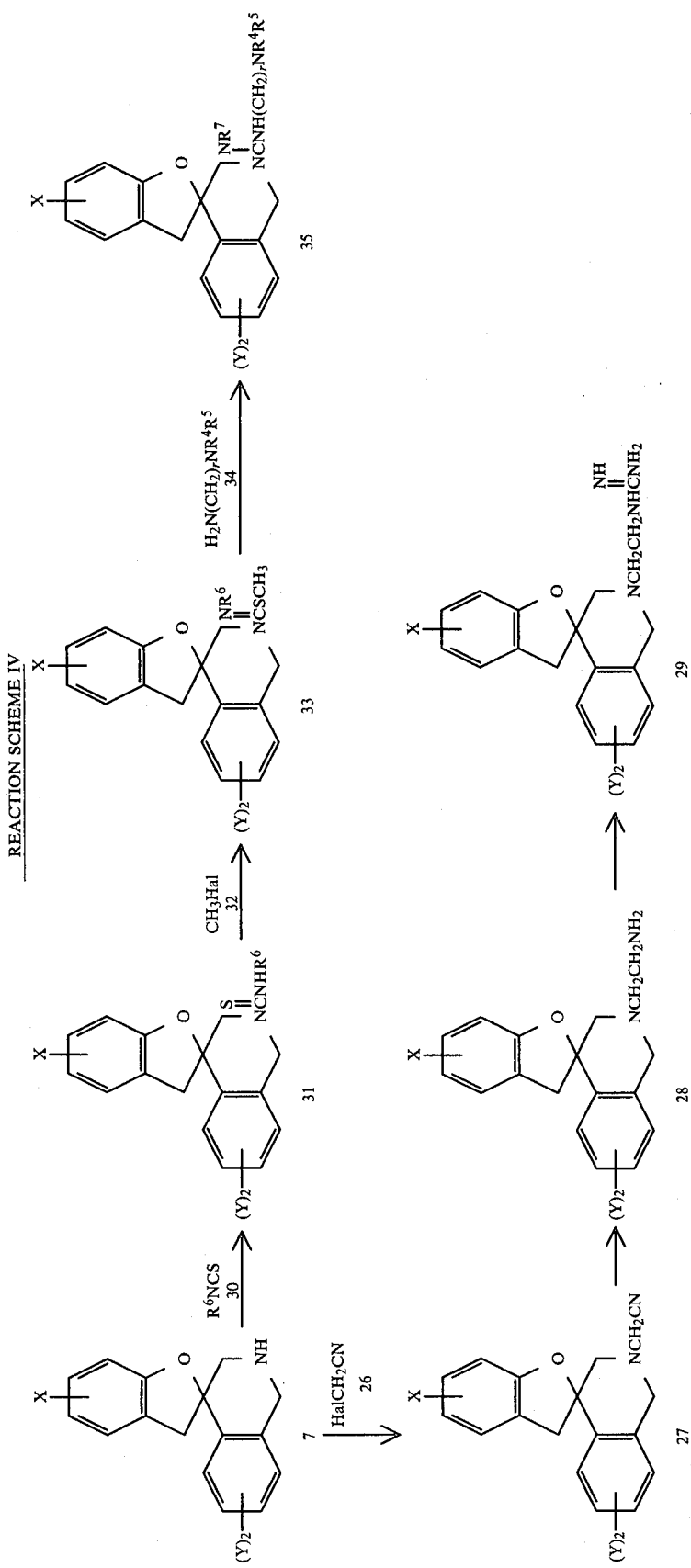

REACTION SCHEME V

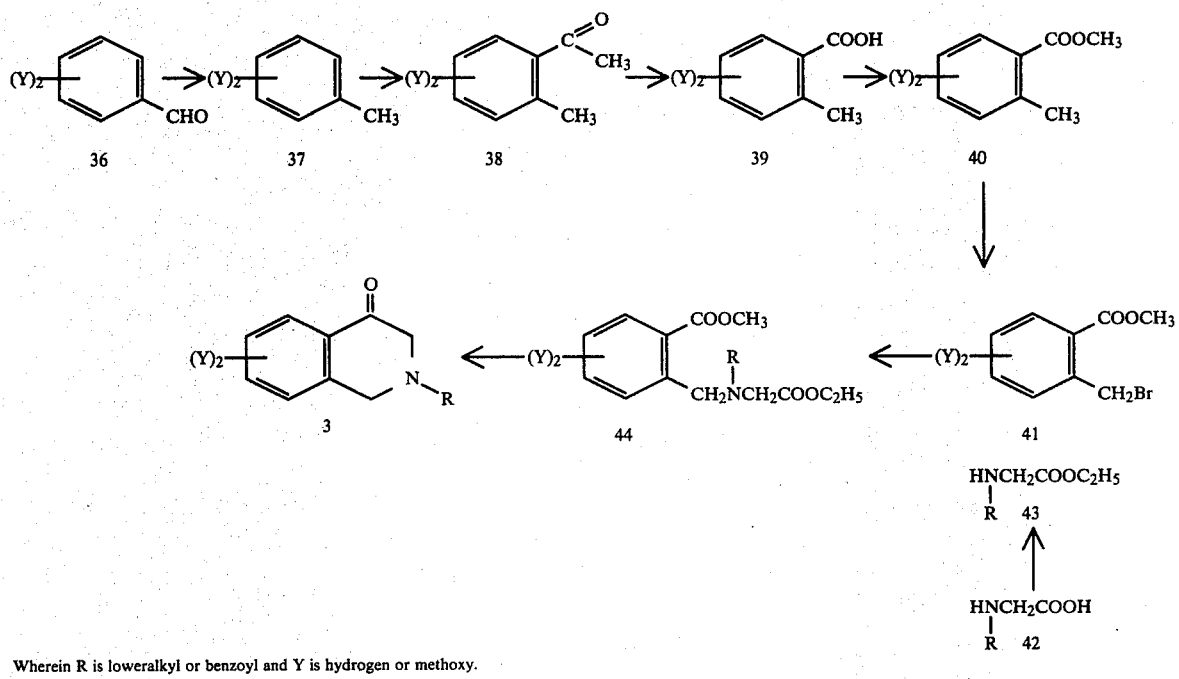

Wherein R is loweralkyl or benzoyl and Y is hydrogen or methoxy.

REACTION SCHEME VI

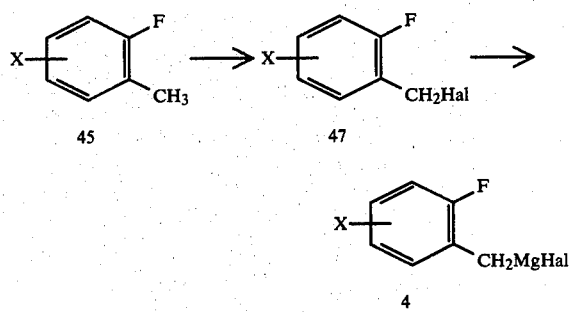

Wherein X is hydrogen or halogen and Hal is chloro or bromo.

We claim:
1. A compound of the formula

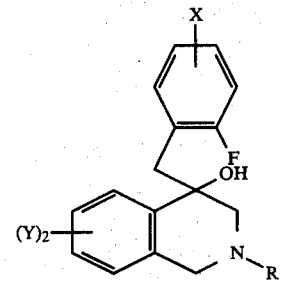

wherein R is loweralkyl or benzyl; X is hydrogen or halogen; Y is hydrogen or methoxy.

2. The compound of claim 1 wherein X is chloro or fluoro.

3. The compound of claim 2 which is 2-benzyl-4-(2-fluorobenzyl)-1,2,3,4-tetrahydro-4-isoquinolinol.

4. The compound of claim 2 which is 4-(2-fluorobenzyl)-2-methyl-1,2,3,4-tetrahydro-4-isoquinolinol.

5. The compound of claim 2 which is 4-(2-fluorobenzyl)-6,7-dimethoxy-2-methyl-1,2,3,4-tetrahydro-4-isoquinolinol].

6. The compound of claim 2 which is 4-(4-chloro-2-fluorobenzyl)-2-methyl-1,2,3,4-tetrahydro-4-isoquinolinol.

* * * * *

UNITED STATES PATENT AND TRADEMARK OFFICE
CERTIFICATE OF CORRECTION

PATENT NO. : 4,410,699

DATED : October 18, 1983

INVENTOR(S) : Richard C. Effland; Larry Davis; Joseph T. Klein

It is certified that error appears in the above-identified patent and that said Letters Patent is hereby corrected as shown below:

Column 8, Line 35

"now" should be -- not --

Column 10, Line 41

"metod" should be -- method --

Column 14, Line 21

"for" should be -- or --

Column 18, Line 13

"hydrocholoride" should be -- hydrochloride --

Column 22, Line 53

"50 ml)" should be -- (50 ml) --

UNITED STATES PATENT AND TRADEMARK OFFICE
CERTIFICATE OF CORRECTION

PATENT NO. : 4,410,699

DATED : October 18, 1983

INVENTOR(S) : Richard C. Effland; Larry Davis; Joseph T. Klein

It is certified that error appears in the above-identified patent and that said Letters Patent is hereby corrected as shown below:

Column 29, Line 20

"(10.6g), 83%)"  should be  -- (10.6g, 83%) --

Column 29, Line 54

"2'-(Guanidinoethyl)spiro[benzofuran-2(3H),4'(2'H)isoquinoline] hemisulfate"  should be -- 2'-(2-Guanidinoethyl)spiro benzofuran-2(3H),4'(2'H) isoquinoline hemisulfate --

Signed and Sealed this

Twenty-fourth Day of January 1984

[SEAL]

Attest:

GERALD J. MOSSINGHOFF

Attesting Officer

Commissioner of Patents and Trademarks